(12) United States Patent
Metcalfe et al.

(10) Patent No.: US 11,998,450 B2
(45) Date of Patent: Jun. 4, 2024

(54) SYSTEMS AND METHODS OF FORMING ORTHOPAEDIC IMPLANTS INCLUDING PRINTED AUGMENTS

(71) Applicant: Arthrex, Inc., Naples, FL (US)

(72) Inventors: Nick Metcalfe, Bonita Springs, FL (US); Michael Moreland, Fort Myers, FL (US); Chris Cronin, Bonita Springs, FL (US)

(73) Assignee: ARTHREX, INC., Naples, FL (US)

( * ) Notice: Subject to any disclaimer, the term of this patent is extended or adjusted under 35 U.S.C. 154(b) by 123 days.

(21) Appl. No.: 17/203,988

(22) Filed: Mar. 17, 2021

(65) Prior Publication Data

US 2021/0307911 A1    Oct. 7, 2021

Related U.S. Application Data

(60) Provisional application No. 63/003,468, filed on Apr. 1, 2020.

(51) Int. Cl.
*A61F 2/30*    (2006.01)
*A61F 2/40*    (2006.01)
*B33Y 80/00*    (2015.01)

(52) U.S. Cl.
CPC ...... *A61F 2/30942* (2013.01); *A61F 2/30734* (2013.01); *A61F 2/30749* (2013.01); *A61F 2/4081* (2013.01); *B33Y 80/00* (2014.12); *A61F 2002/30011* (2013.01); *A61F 2002/30616* (2013.01); *A61F 2002/30952* (2013.01); *A61F 2002/30985* (2013.01); *A61F 2002/4085* (2013.01)

(58) Field of Classification Search
CPC ............................... B33Y 80/00; B33Y 30/00
See application file for complete search history.

(56) References Cited

U.S. PATENT DOCUMENTS

| | | | |
|---|---|---|---|
| 7,931,690 B1 | 4/2011 | Bonutti | |
| 7,993,408 B2 * | 8/2011 | Meridew | ............... A61F 2/4081 623/22.32 |
| 8,303,665 B2 | 11/2012 | Tornier et al. | |
| 8,632,597 B2 | 1/2014 | Lappin | |
| 8,843,229 B2 | 9/2014 | Vanasse et al. | |

(Continued)

FOREIGN PATENT DOCUMENTS

| | | | |
|---|---|---|---|
| EP | 3403617 | 11/2018 | |
| EP | 3415108 A1 * | 12/2018 | ............. A61B 17/80 |

(Continued)

OTHER PUBLICATIONS

Musculoskeletal Key. Arthrex Univers Revers (TM) shoulder prosthesis. Retrieve from: https://musculoskeletalkey.com/arthrex-univers-revers-shoulder-prosthesis/.

(Continued)

*Primary Examiner* — Cachet I Proctor
(74) *Attorney, Agent, or Firm* — Carlson, Gaskey & Olds, P.C.

(57) ABSTRACT

This disclosure relates to orthopaedic implants and methods for repairing bone defects and restoring functionality to a joint. The implants and methods disclosed herein include augments formed on respective baseplates. The augments may have geometries that may approximate a surface contour or bone void along a surgical site.

20 Claims, 19 Drawing Sheets

(56) References Cited

U.S. PATENT DOCUMENTS

| | | | |
|---|---|---|---|
| 8,852,283 B2 | 10/2014 | Tornier et al. |
| 8,940,054 B2 | 1/2015 | Wiley et al. |
| 9,114,017 B2 | 8/2015 | Lappin |
| 9,226,830 B2 | 1/2016 | De Wilde et al. |
| 9,233,003 B2 | 1/2016 | Rouche et al. |
| 9,283,083 B2 | 3/2016 | Winslow et al. |
| 9,452,055 B2 | 9/2016 | Lappin |
| 9,532,880 B2 | 1/2017 | Lappin |
| 9,545,312 B2 | 1/2017 | Tornier et al. |
| 9,629,725 B2 | 4/2017 | Gargac et al. |
| 9,844,440 B2 | 12/2017 | Kovacs et al. |
| 10,016,811 B2 | 7/2018 | Neal |
| 10,034,757 B2 | 7/2018 | Kovacs et al. |
| 10,265,184 B2 | 4/2019 | Lappin |
| 10,357,373 B2 | 7/2019 | Gargac et al. |
| 10,383,735 B2 | 8/2019 | Wiley et al. |
| 2006/0241776 A1* | 10/2006 | Brown | A61B 17/7225 623/22.32 |
| 2012/0016485 A1* | 1/2012 | Sharp | A61F 2/4609 623/22.21 |
| 2012/0089235 A1* | 4/2012 | Conway | A61B 17/8066 623/22.32 |
| 2014/0257499 A1* | 9/2014 | Winslow | A61F 2/4081 623/19.13 |
| 2015/0305877 A1* | 10/2015 | Gargac | A61F 2/4081 623/19.11 |
| 2016/0045323 A1* | 2/2016 | Kovacs | A61F 2/4081 623/19.11 |
| 2016/0310285 A1* | 10/2016 | Kovacs | A61B 17/1778 |
| 2017/0095336 A1 | 4/2017 | Tornier et al. |
| 2017/0249440 A1 | 8/2017 | Lang et al. |
| 2018/0049878 A1* | 2/2018 | Stulberg | A61F 2/389 |
| 2018/0303618 A1 | 10/2018 | Kovacs et al. |
| 2018/0333263 A1* | 11/2018 | Roby | A61F 2/4081 |
| 2018/0333268 A1 | 11/2018 | Cardon et al. |
| 2019/0015116 A1 | 1/2019 | Gargac et al. |
| 2019/0015117 A1 | 1/2019 | Neichel et al. |
| 2019/0015118 A1 | 1/2019 | Neichel et al. |
| 2019/0015221 A1* | 1/2019 | Neichel | A61F 2/4081 |
| 2019/0151106 A1 | 5/2019 | Kovacs et al. |
| 2019/0159907 A1 | 5/2019 | Roche et al. |
| 2019/0240035 A1 | 8/2019 | Lappin |
| 2019/0298537 A1 | 10/2019 | Gargac et al. |
| 2021/0307919 A1* | 10/2021 | Paterson | A61F 2/30771 |

FOREIGN PATENT DOCUMENTS

| | | | |
|---|---|---|---|
| EP | 3498227 | 6/2019 | |
| WO | 2012141790 | 10/2012 | |
| WO | 2017007565 | 1/2017 | |
| WO | WO-2017007565 A2 * | 1/2017 | ......... A61B 17/8605 |
| WO | 2017165346 | 9/2017 | |
| WO | 2018052965 | 3/2018 | |
| WO | 2018081073 | 5/2018 | |
| WO | 2019033037 | 2/2019 | |

OTHER PUBLICATIONS

International Search Report for International Application No. PCT/US2021/022677 dated Jun. 25, 2021.

International Preliminary Report on Patentability for International Application No. PCT/US2021/022677 dated Oct. 13, 2022.

* cited by examiner ary tool.

SYSTEMS AND METHODS OF FORMING ORTHOPAEDIC IMPLANTS INCLUDING PRINTED AUGMENTS

CROSS-REFERENCE TO RELATED APPLICATIONS

This application claims priority to provisional application 63/003,468, filed on Apr. 1, 2020, incorporated by reference herein in its entirety.

BACKGROUND

This disclosure relates to orthopaedic procedures and, more particularly, to orthopaedic implants and methods for repairing bone defects and restoring functionality to a joint.

Many bones of the human musculoskeletal system include articular surfaces. The articular surfaces articulate relative to other bones to facilitate different types and degrees of joint movement. The articular surfaces can erode or experience bone loss over time due to repeated use or wear or can fracture as a result of a traumatic impact. These types of bone defects can cause joint instability and pain.

Bone deficiencies may occur along the articular surfaces of the glenoid bone. Some techniques utilize a bone graft and/or implant to fill a defect in the glenoid bone. The implant may be secured to the glenoid utilizing one or more fasteners.

SUMMARY

This disclosure relates to orthopaedic implants and methods. The implants may be used during methods for repairing bone defects. The implants described herein may be utilized to restore functionality to a joint and include augments formed on respective baseplates having apertures that receiving fasteners to secure the implants at a surgical site.

A method of forming an orthopaedic implant of the present disclosure may include defining an augment volume associated with a respective baseplate. The baseplate may include a plate body extending between front and rear faces and may include at least one plate aperture extending along an aperture axis between the front and rear faces. A void space in the augment volume may be defined along a trajectory of the aperture axis. The method may include printing an augment on the rear face of the respective baseplate according to the augment volume such that at least one augment aperture is established in the void space along the trajectory of the respective aperture axis.

An orthopaedic implant of the present disclosure may include a baseplate including a plate body and at least one plate aperture extending along an aperture axis between front and rear faces of the plate body. A predefined augment volume may be dimensioned to extend between the rear face and a predefined surface contour of a bone surface. A void space may be established in the predefined augment volume along a trajectory of the respective aperture axis. The implant may include an augment printed on the rear face according to the predefined augment volume such that a respective augment aperture of the augment is established along the trajectory of the aperture axis.

A kit for arthroplasty of the present disclosure may include a set of implants and a plurality of fasteners. Each implant in the set of implants may include a baseplate including a plate body and a plurality of plate apertures extending along respective aperture axes between front and rear faces of the plate body. Each implant may include an augment printed on the rear face of the baseplate according to a predefined augment volume such that augment apertures are established in the augment along a trajectory of respective ones of the aperture axes. The plate apertures and the augment apertures may be dimensioned to receive respective ones of the fasteners to secure the implant to bone.

The various features and advantages of this disclosure will become apparent to those skilled in the art from the following detailed description. The drawings that accompany the detailed description can be briefly described as follows.

BRIEF DESCRIPTION OF THE DRAWINGS

Like reference numbers and designations in the various drawings indicate like elements.

DETAILED DESCRIPTION

Figure 1:
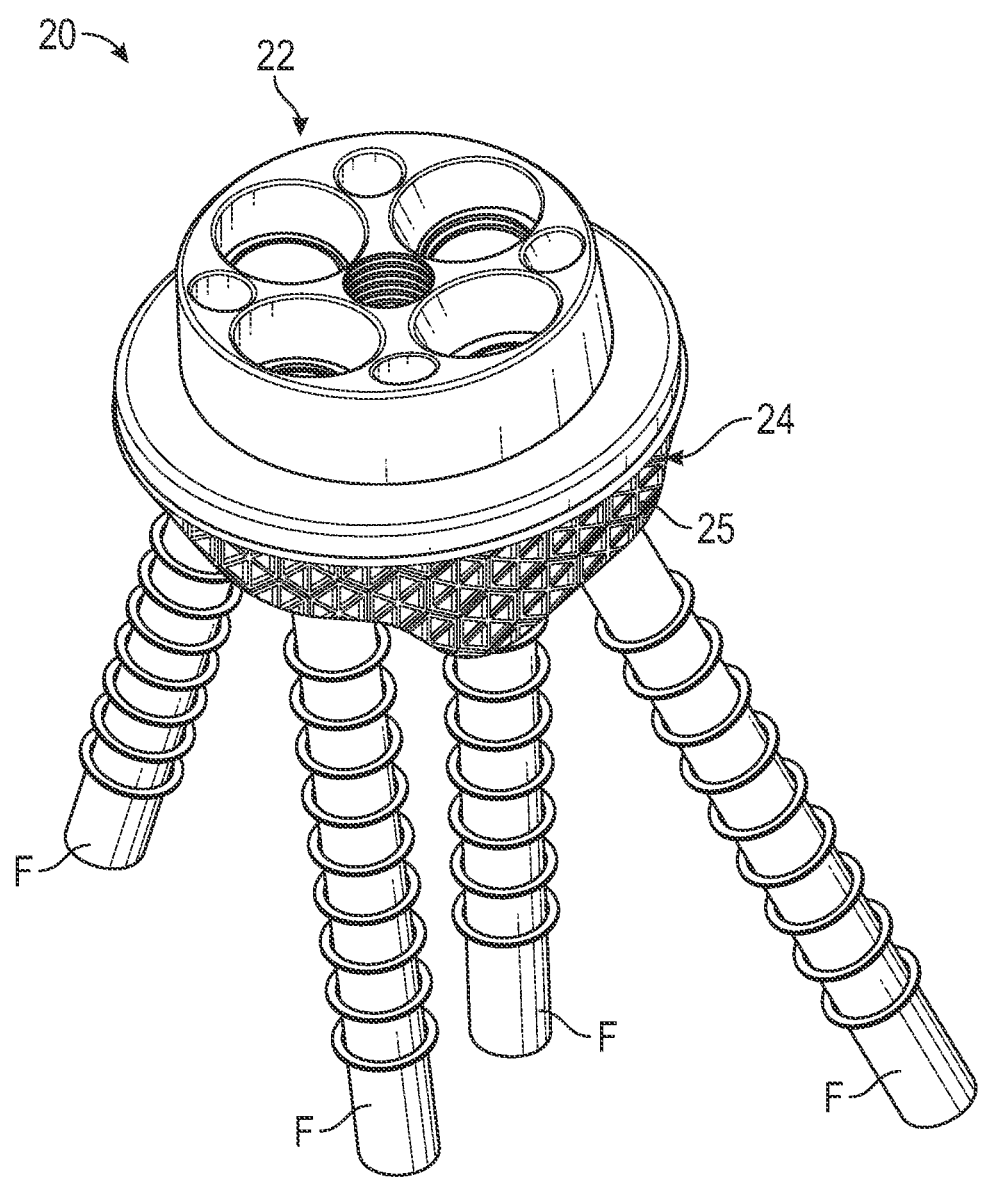
FIGS. 1-1A illustrate a perspective view of an exemplary orthopaedic implant including a baseplate and implant.

This disclosure relates to orthopaedic implants and methods for repairing bone defects. The implants described herein may be utilized during arthroplasty procedures and incorporated into a shoulder prosthesis for restoring functionality to shoulders having advanced cartilage disease. The disclosed implants may be utilized to address complex glenoid pathology, which may have bony deficiencies at many different orientations relative to the Superior/Inferior (S/I) plane of the glenoid face. The implants may include augments formed on a respective baseplate that correspond to or approximate a patient-specific contour along a surgical site such as the glenoid face to fill a bone void, which may lead to improved healing by ensuring sufficient contact and fixation. The augment may be formed utilizing additive manufacturing or three-dimensional (3D) printing techniques.

A method of forming an orthopaedic implant for implanting in a patient according to an exemplary aspect of the present disclosure may include defining an augment volume associated with a respective baseplate. The baseplate may include a plate body extending between front and rear faces and may include at least one plate aperture extending along an aperture axis between the front and rear faces. A void space in the augment volume may be defined along a trajectory of the aperture axis. The method may include printing an augment on the rear face of the respective baseplate according to the augment volume such that at least one augment aperture may be established in the void space along the trajectory of the respective aperture axis.

In some embodiments, the at least one plate aperture may include a plurality of plate apertures distributed along the rear face, and the at least one augment aperture may include a plurality of augment apertures aligned with respective ones of the plate apertures.

In some embodiments, each of the plate apertures and a respective one of the augment apertures may be dimensioned to receive a common fastener along the respective plate aperture axis.

In some embodiments, the printing step may include establishing an augment body of the augment along the rear face and establishing an anchoring stem of the augment that extends outwardly from the augment body.

In some embodiments, the printing step may occur such that the augment apertures may be circumferentially distributed about a longitudinal axis of the anchoring stem.

In some embodiments, the printing step may occur such that at least a portion of a medial face of the augment may be transverse to the rear face, and the at least one augment aperture may extend between the portion of the medial face and a lateral face of the augment disposed along the rear face of the plate body.

In some embodiments, the rear face may have a substantially planar geometry, and the aperture axis may be non-perpendicular to the rear face.

In some embodiments, the augment volume may be defined between the rear face of the respective baseplate and a predefined surface contour of a bone surface.

In some embodiments, the method may include determining the predefined surface contour prior to the defining step, and the predefined surface contour may be a patient-specific surface contour of a glenoid face.

In some embodiments, the method may include positioning the respective baseplate in a fixture such that the rear face may be exposed, and the printing step may include moving a printing head across the rear face.

In some embodiments, the method may include repeating the defining and printing steps for a first set of baseplates, and the positioning step may include positioning the first set of baseplates at respective locations along the fixture.

In some embodiments, the rear face may have a substantially planar geometry.

In some embodiments, the defining step may occur such that the augment volume associated with a baseplate of the first set of baseplates may differ from the augment volume associated with another baseplate of the first set of baseplates.

In some embodiments, the method may include repeating the defining and printing steps for a second set of baseplates, the positioning step may include positioning the second set of baseplates at respective locations along the fixture, and the defining step may occur such that the augment volume may be common to each augment corresponding to the second set of baseplates.

In some embodiments, the plate body may comprise a first material, the augment may comprise a second material, and the printing step may occur such that a porosity of the second material may differ from a porosity of the first material.

In some embodiments, the printing step may occur such that augment may include a porous scaffold having an interconnected network of branches and nodes, and the method may include positioning biological material in the porous scaffold.

In some embodiments, the method may include securing a glenosphere to the plate body adjacent to the front face, and the glenosphere may include an articulating surface that may have a generally convex geometry.

In some embodiments, the glenosphere may include a recess dimensioned to at least partially receive the plate body, the plate body may include a mounting portion establishing the front face, and a perimeter of the mounting portion may be dimensioned to cooperate with a perimeter of the recess to establish a Morse taper connection.

An orthopaedic implant for implanting in a patient according to an exemplary aspect of the present disclosure may include a baseplate including a plate body and at least one plate aperture extending along an aperture axis between front and rear faces of the plate body. A predefined augment volume may be dimensioned to extend between the rear face and a predefined surface contour of a bone surface. A void space may be established in the predefined augment volume along a trajectory of the respective aperture axis. An augment may be printed on the rear face according to the predefined augment volume such that a respective augment aperture of the augment may be established along the trajectory of the aperture axis.

In some embodiments, the predefined surface contour may be a patient-specific surface contour of a glenoid face.

A kit for arthroplasty according to an exemplary aspect of the present disclosure may include a set of implants and a plurality of fastener. Each implant in the set of implants may include a baseplate including a plate body and a plurality of plate apertures extending along respective aperture axes between front and rear faces of the plate body. An augment may be printed on the rear face of the baseplate according to a predefined augment volume such that augment apertures may be established in the augment along a trajectory of respective ones of the aperture axes. The plate apertures and the augment apertures may be dimensioned to receive respective ones of the fasteners to secure the implant to bone.

In some embodiments, the set of implants may include a first set of baseplates and a second set of baseplates. The predefined augment volume associated with a baseplate of the first set of baseplates may differ from the predefined augment volume associated with another baseplate of the first set of baseplates. The predefined augment volume associated with each baseplate of the second set of baseplates may be common to the second set of baseplates.

In some embodiments, the predefined augment volume may correspond to a respective patient-specific surface contour such that at least some augments in the set of implants may differ in geometry.

Figure 1A:
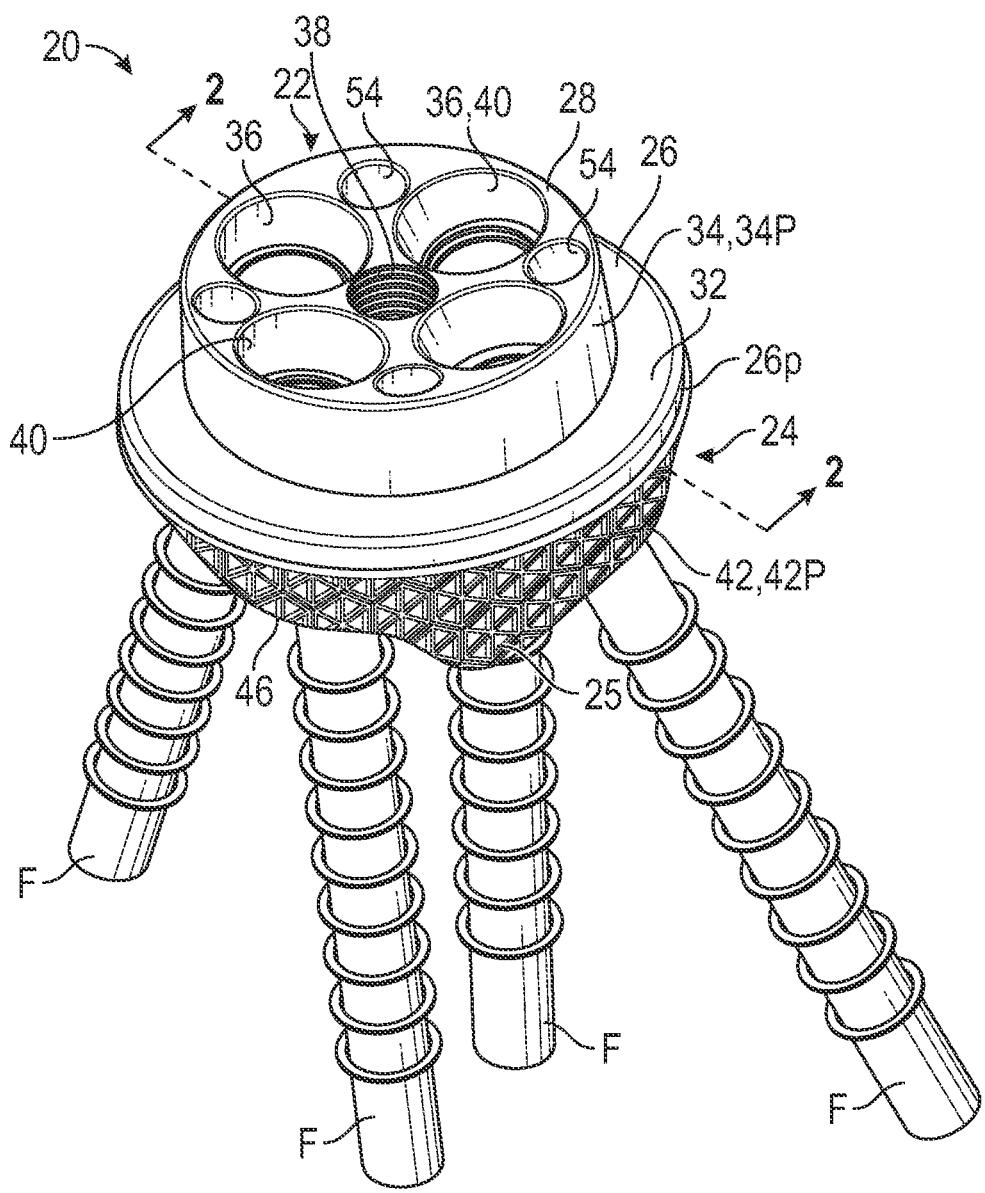
Figure 2:
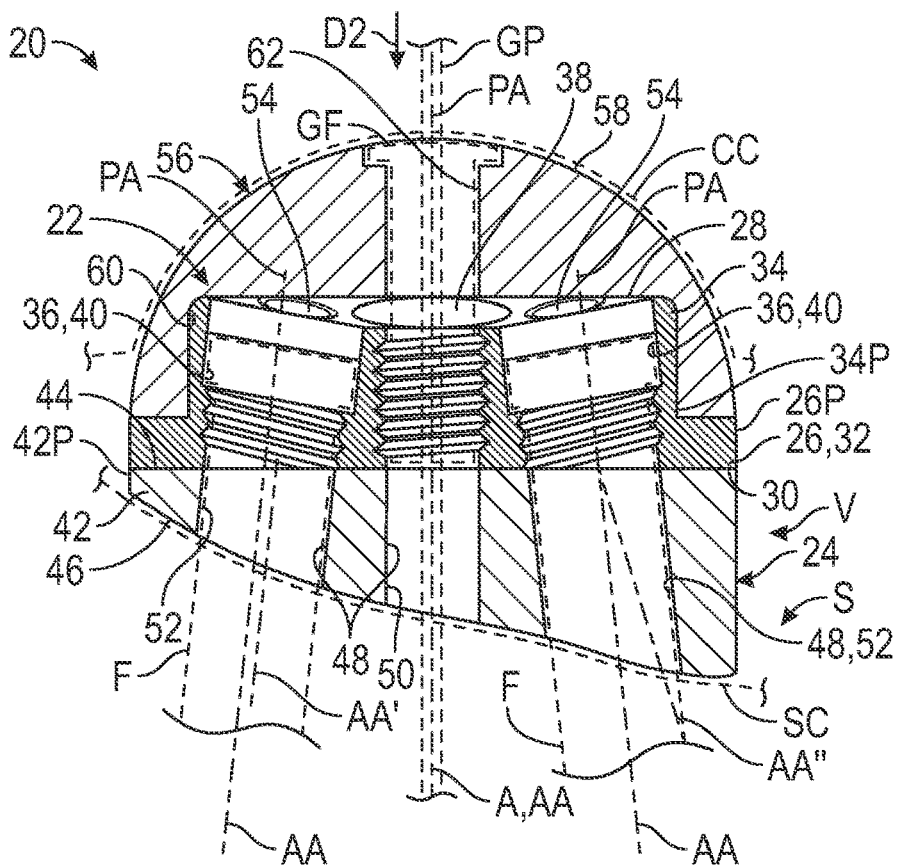
FIG. 2 illustrates a sectional view of the implant taken along line 1-1 of FIG. 1A including a glenosphere in an installed position.

FIGS. 1-1A and 2 illustrate an exemplary orthopedic implant 20 for implanting in a patient according to an embodiment. The implant 20 can be utilized for various surgical procedures, such as arthroplasty procedures to repair a joint. For example, the implant 20 can be incorporated into a shoulder prosthesis. Although the implants disclosed herein primarily refer to repair of a defect in a glenoid during a shoulder reconstruction, such as a reverse shoulder procedure, it should be understood that the disclosed implants may be utilized in other locations of the patient and other surgical procedures including repair of other joints such as a wrist, hand, hip, knee or ankle, and including repair of fractures. The implant 20 includes a baseplate 22 and an augment 24. The augment 24 can be separately formed along the baseplate 22.

Referring to FIGS. 1A and 2, the baseplate 22 includes a plate body 26 extending along a central axis A (FIG. 2) between a front (or first) face 28 and a rear (or second) face 30 (FIG. 2) generally opposed to the front face 28.

The plate body 26 includes a base portion 32 and a mounting portion 34 extending outwardly from the base portion 32. The base portion 32 may be an annular flange extending about a perimeter 34P of the mounting portion 34 to establish a perimeter 26P of the plate body 26, as illustrated in FIGS. 1A and 2. The perimeter 26P of the plate body 26 can have various geometries, such as a generally rectangular, elliptical, oval, oblong or complex geometry. The perimeter 26P of the plate body 26 may have a substantially circular geometry, as illustrated in FIGS. 1A and 2. For the purposes of this disclosure, the terms "substantially" and "approximately" mean±5% of the stated relationship or value unless otherwise stated. A substantially circular geometry may reduce a reaming width and complexity of preparing a surgical site to accept the implant 20. The mounting portion 34 establishes the front face 28, and the base portion 32 establishes the rear face 30 of the plate body 26.

The baseplate 22 includes at least one plate aperture (or hole) 36 in a thickness of the plate body 26. The baseplate 22 may include a plurality of plate apertures 36 distributed between the front and rear faces 28, 30, as illustrated in FIGS. 1A and 2. The plate apertures 36 include a central aperture 38 and one or more peripheral apertures 40 extending along respective aperture axes PA (FIG. 2) between the front and rear faces 28, 30 of the plate body 26. The central aperture 38 may be dimensioned to extend along the central axis A of the baseplate 22. The central aperture 38 may be dimensioned such that the respective aperture axis PA is substantially collinear with the central axis A. The respective aperture axes PA of the peripheral apertures 40 can be substantially parallel to the central axis A as illustrated by the central aperture 38, or can be transverse to the central axis A as illustrated by the peripheral apertures 40 of FIG. 2.

Referring to FIG. 2, with continuing reference to FIG. 1A, the augment 24 may be disposed on and extend from the rear face 30 of the baseplate 22. The augment 24 includes an augment body 42 extending along the central axis A between a front (or first) face 44 and a rear (or second) face 46. The rear faces 30, 46 of the baseplate 22 and augment 24 may generally correspond to a medial side of a patient, and the front faces 28, 44 of the baseplate 22 and augment 24 may generally correspond to a lateral side of the patient when implanted in a surgical site S, for example.

Figures 3, 4:
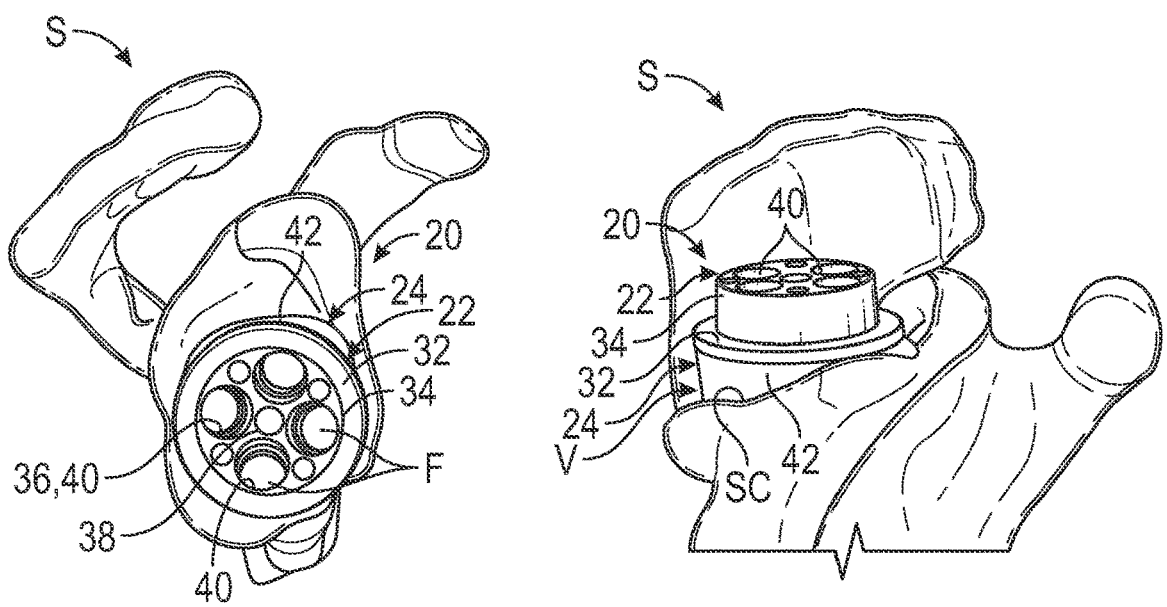
FIGS. 3-4 illustrate views of the implant of FIG. 1 situated relative to a surgical site.

The augment 24 can be dimensioned to approximate various defect geometries and surface contours that may be encountered along a surgical site S. The rear face 46 of the augment 24 may be dimensioned to contact tissue T such as bone along the surgical site S. A bone surface along the surgical site S may establish or be characterized by a predefined surface contour SC. The predefined surface contour SC may be a patient-specific surface contour of a glenoid face, and the implant 20 may be secured to the glenoid face along the patient-specific surface contour SC as illustrated in FIGS. 3-4.

The augment 24 can have various geometries to at least partially fill a bone void or augment volume V between the baseplate 22 and the predefined surface contour SC of the bone surface.

A geometry of the rear face 46 of the augment 24 can be the same or can differ from a geometry of the rear face 30 of the baseplate 22. For example, the rear face 30 of the baseplate 22 can have a substantially planar geometry that is perpendicular to the central axis A, and a cross section of the augment body 42 can have a generally or substantially wedge-shaped geometry that extends across a full width of the plate body 26 (e.g., "full-wedge"), as illustrated by FIG. 2. The rear face 46 can be substantially planar, or can have one more concave or convex sections that complements a geometry of the respective surface contour SC.

The rear face 46 of the augment 24 may slope between opposed sides of a perimeter 42P of the augment body 42 such that substantially all (or at least a portion) of the rear face 46 of the augment 24 is transverse to the rear face 30 of the baseplate 22. The rear face 46 may be arranged transversely relative to the central axis A and may be dimensioned such that innermost (e.g., lowest) and outermost (e.g., highest) points of the rear face 46 relative to the central axis A are defined along the perimeter 42P of the augment body 42, as illustrated in FIG. 2. The augment body 42 can have other shaped or profiles, such as a generally step-shaped geometry.

The augment 24 may include at least one augment aperture (or hole) 48 in a thickness of the augment body 42. Each augment aperture 48 can be dimensioned with respect to one or more aspects of the baseplate 22. The augment 24 can include a plurality of augment apertures 48 distributed between the front and rear faces 44, 46 of the augment body 42, as illustrated in FIG. 2. The augment apertures 48 can include a central augment aperture 50 and one or more peripheral augment apertures 52 extending along respective augment aperture axes AA between the front and rear faces 44, 46 of the augment body 42.

The augment apertures 48 can be dimensioned with respect to the plate apertures 36. For example, the augment 24 can be dimensioned such that a respective augment aperture 48 is established along a trajectory of the aperture axis PA of at least some of the plate apertures 36 and such that a projection of the aperture axis PA intersects the respective augment aperture 48. A respective augment aperture 48 may be established along a trajectory of the aperture axis PA of each of the plate apertures 36 such that the augment aperture axis AA is substantially collinear with the respective aperture axis PA, as illustrated in FIG. 2. The augment aperture axis AA may be parallel or transverse to the respective aperture axis PA, as illustrated by augment aperture axes AA', AA" of FIG. 2, respectively. The aperture axis PA of each peripheral aperture 40 can be substantially perpendicular to the rear face 30 (see, e.g., implant 320-1 of FIG. 27B) or can be non-perpendicular to the rear face 30 as illustrated in FIG. 2.

The apertures 36, 48 can be dimensioned to receive a K-wire or guide pin GP, as illustrated by the central apertures 38, 50 of FIG. 2 (GP shown in dashed lines for illustrative purposes). For example, the guide pin GP can be situated in the tissue T during preparation and/or placement of the implant 20 at the surgical site S.

Each plate aperture 36 may be dimensioned to receive a respective fastener F, as illustrated in FIG. 1A (also shown in dashed lines in FIG. 2 for illustrative purposes). Each of the plate apertures 36 and a respective one of the augment apertures 48 can be dimensioned to receive a common fastener F along the respective plate aperture axis PA for securing the baseplate 22 to the tissue T at the surgical site S, as illustrated by the peripheral apertures 40 and peripheral augment apertures 52 in FIG. 2. Example fasteners may include pins, nails, bolts, and compression screws as illustrated by the fasteners F of FIG. 1.

The baseplate 22 can include one or more recesses 54 extending inwardly from the front face 28 of the plate body 26. The recesses 54 can be dimensioned to receive an inserter or tooling to insert or otherwise position the baseplate 22 along the surgical site S. The recesses 54 may be omitted.

The implant 20 can include a glenosphere 56 releasably securable to the baseplate 22. The glenosphere 56 includes an articulating surface 58 which may have a generally convex geometry. The articulating surface 58 may cooperate with an articulating surface CC such as a humeral component having a generally concave, complementary geometry (shown in dashed lines for illustrative purposes). The front face 28 of the baseplate 22 can have a generally concave geometry, as illustrated in FIG. 2. The glenosphere 56 may be omitted and the front face 28 may serve as an articulating surface that cooperates with a humeral component having a generally convex, complementary geometry. Features of the glenosphere 56 can be incorporated into any of the baseplates disclosed herein. For example, the front face 28 of the baseplate 22 can be dimensioned to establish the articulating surface 58 which may have a generally convex geometry, and may include one or more plate apertures (or holes) defined in a respective flanged section which may extend outwardly from a respective plate body, as illustrated by the plate apertures 136, 236 and flanged section 135, 235 of the baseplates 122, 222 of FIGS. 5-8.

The glenosphere 56 can be mechanically attached or releasably secured to the baseplate 22 adjacent to the front face 28. The glenosphere 56 may include a recess 60 dimensioned to at least partially receive the mounting portion 34 of the plate body 26 adjacent to the front face 28. The recess 60 may be dimensioned to encircle a rim or perimeter 34P of the mounting portion 34 of the baseplate 22 along the front face 28. The perimeter 34P can be dimensioned to cooperate with a perimeter of the recess 60 to establish a Morse taper connection to secure the glenosphere 56 to the baseplate 22, as illustrated in FIG. 2. The glenosphere 56 can be impacted or pressed on the mounting portion 34 to establish an interference fit or otherwise seat the glenosphere 56.

The glenosphere 56 can include an aperture 62 dimensioned to receive a fastener GF (shown in dashed lines for illustrative purposes). The fastener GF can include threading that cooperates with threading along the central aperture 38 of the baseplate 22. The fastener GF can serve to align the glenosphere 56 relative to the central axis A during assembly and/or secure the glenosphere 56 to the baseplate 24. The fastener CF and/or apertures 38, 62 may be omitted.

Various materials can be utilized to form the implant 20 including the baseplate 22, augment 24 and glenosphere 56. The baseplate 22, augment 24 and glenosphere 56 can be made of surgical grade metallic materials. Example metallic materials include titanium alloys such as Ti6A14V and cobalt-based materials such as cobalt-chromium (CoCr).

The plate body 26 of the baseplate 22 comprises a first material, and the augment body 42 of the augment 24 comprises a second material. The first and second materials can be same or can differ in composition and/or construction. For example, a porosity of the first and second materials can be same or can differ. For the purposes of this disclosure, the porosity is taken as an average across a total volume of the respective component. The augment 24 may be printed on the baseplate 22 such that the porosity of the second material is greater than the porosity of the first material. The porosity of the second material of the augment 24 can be between approximately 40-80%, or more narrowly between approximately 55-65%.

The augment 24 may be substantially solid or may be porous. For example, the augment 24 may include a porous scaffold 25 having an interconnected network of branches and nodes extending throughout a volume of the augment 24, as illustrated in FIGS. 1-1A. The scaffold 25 can be infused with biological material or biologics to improve healing, as illustrated by the biological material BC and scaffold 325 of FIG. 20. The augment 24 may be substantially solid.

The implant 20 can include one or more coatings or layers deposited along surfaces of the baseplate 22 and/or augment 24. Example coatings can include calcium phosphate (CaP) having a porous construction for promoting bone growth.

Figure 5:
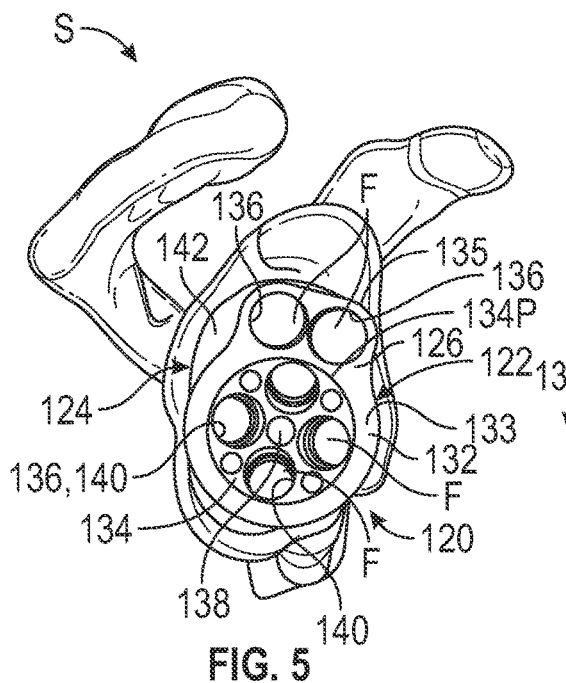
FIGS. 5-6 illustrate an implant according to another embodiment.
Figure 6:
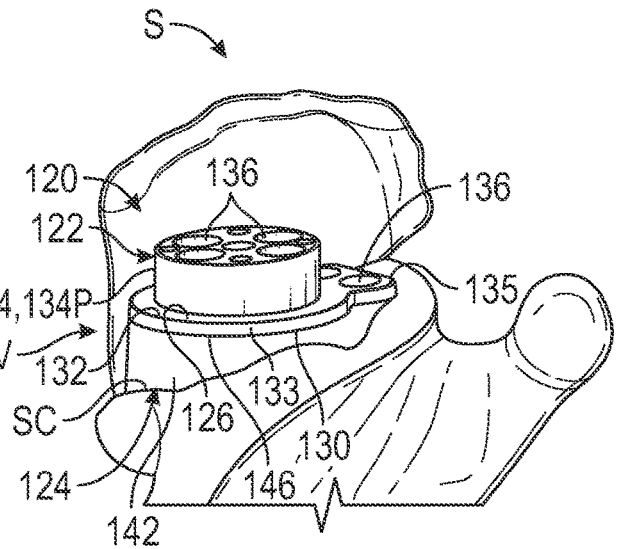

Other baseplate geometries can be utilized. FIGS. 5-6 illustrate another exemplary implant 120 for implanting in a patient. In this disclosure, like reference numerals designate like elements where appropriate and reference numerals with the addition of one-hundred or multiples thereof designate modified elements that are understood to incorporate the same features and benefits of the corresponding original elements.

The implant 120 includes a baseplate 122 and an augment 124. A base portion 132 of the baseplate 122 may include an arcuate-shaped rim section 133 and a flanged section 135. The rim section 133 may follow a perimeter 134P of a mounting portion 134. The flanged section 135 may extend outwardly from the rim section 133. The rim section 133 and flanged section 135 may cooperate to establish a rear face 130 of the baseplate 122, as illustrated in FIG. 6. The flanged section 135 may increase an area of the rear face 130 and a volume V established between the rear face 130 and a facing surface contour SC along a surgical site S. The augment 124 can be dimensioned to extend along the rim and flanged sections 133, 135 of the baseplate 122 to at least partially fill the volume V.

Figure 7:
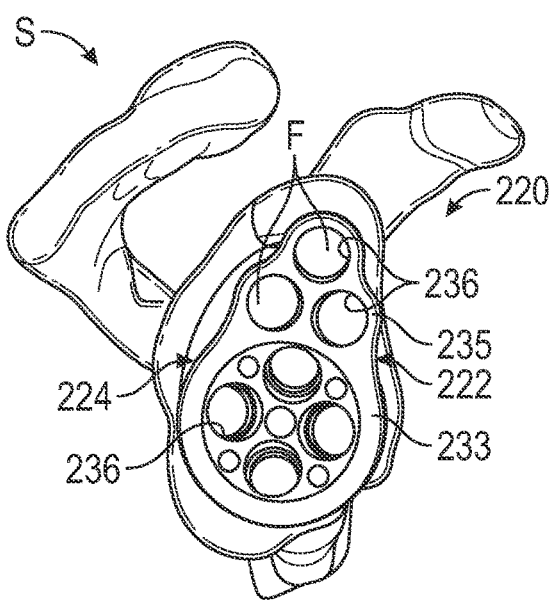
FIGS. 7-8 illustrate an implant according to yet another embodiment.
Figure 8:
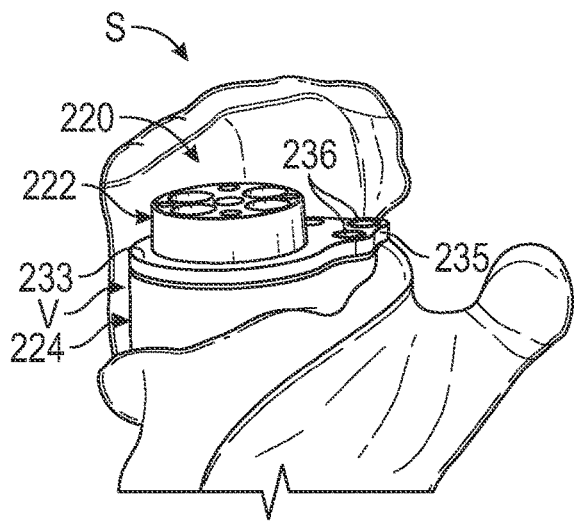

The baseplate 122 includes plate apertures 136 dimensioned to receive respective fasteners F (FIG. 5). The flanged section 135 may include one or more of the plate apertures 136. Fewer or more than two plate apertures 136 can be defined in the flanged section 135. In FIGS. 7-8, baseplate 222 includes a flanged section 235 which may have three plate apertures 236.

Each patient can be associated with a respective patient-specific surface contour along a surgical site. The patient-specific surface contour can establish a bone void or defect, such as along a glenoid face. Various techniques can be utilized to dimension and form orthopaedic implants that generally or substantially approximate the patient-specific surface contours, which can improve healing.

Figure 9:
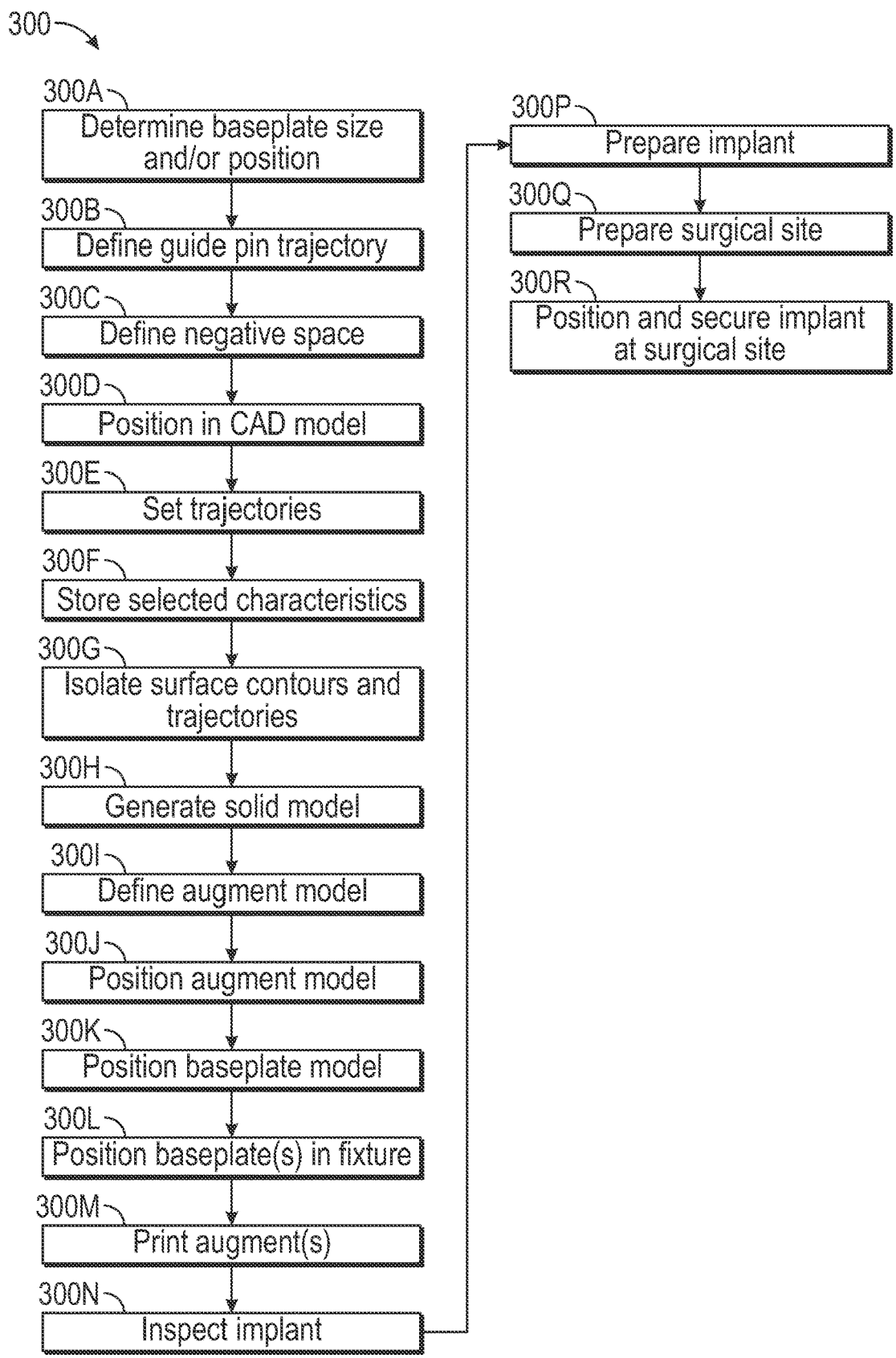
FIG. 9 illustrates an exemplary method of forming an orthopaedic implant.

FIG. 9 illustrates an exemplary method of forming an orthopaedic implant in a flowchart 300. The method may be utilized to form an implant for implanting in a patient and may be utilized in an arthroplasty for restoring functionality to shoulders having advanced cartilage disease, such as repairing bone defects along a glenoid, for example. The method 300 can be utilized with any of the orthopedic implants, baseplate and augment geometries, and aperture arrangements disclosed herein. Although the method 300 primarily refers to implants for repair of a defect in a glenoid during a shoulder reconstruction, it should be understood that the method and disclosed implants may be utilized in other locations of the patient and other surgical procedures. For example, the method may be utilized to form an implant such as a fracture plate dimensioned to span across and secure a bone fracture. The method may be utilized to form an augment on the fracture plate that is dimensioned to substantially follow or approximate a surface contour adjacent the bone fracture and that may include one or more augment apertures for securing the fracture plate. Fewer or additional steps than are recited below could be performed within the scope of this disclosure, and the recited order of steps is not intended to limit this disclosure.

Figure 10:
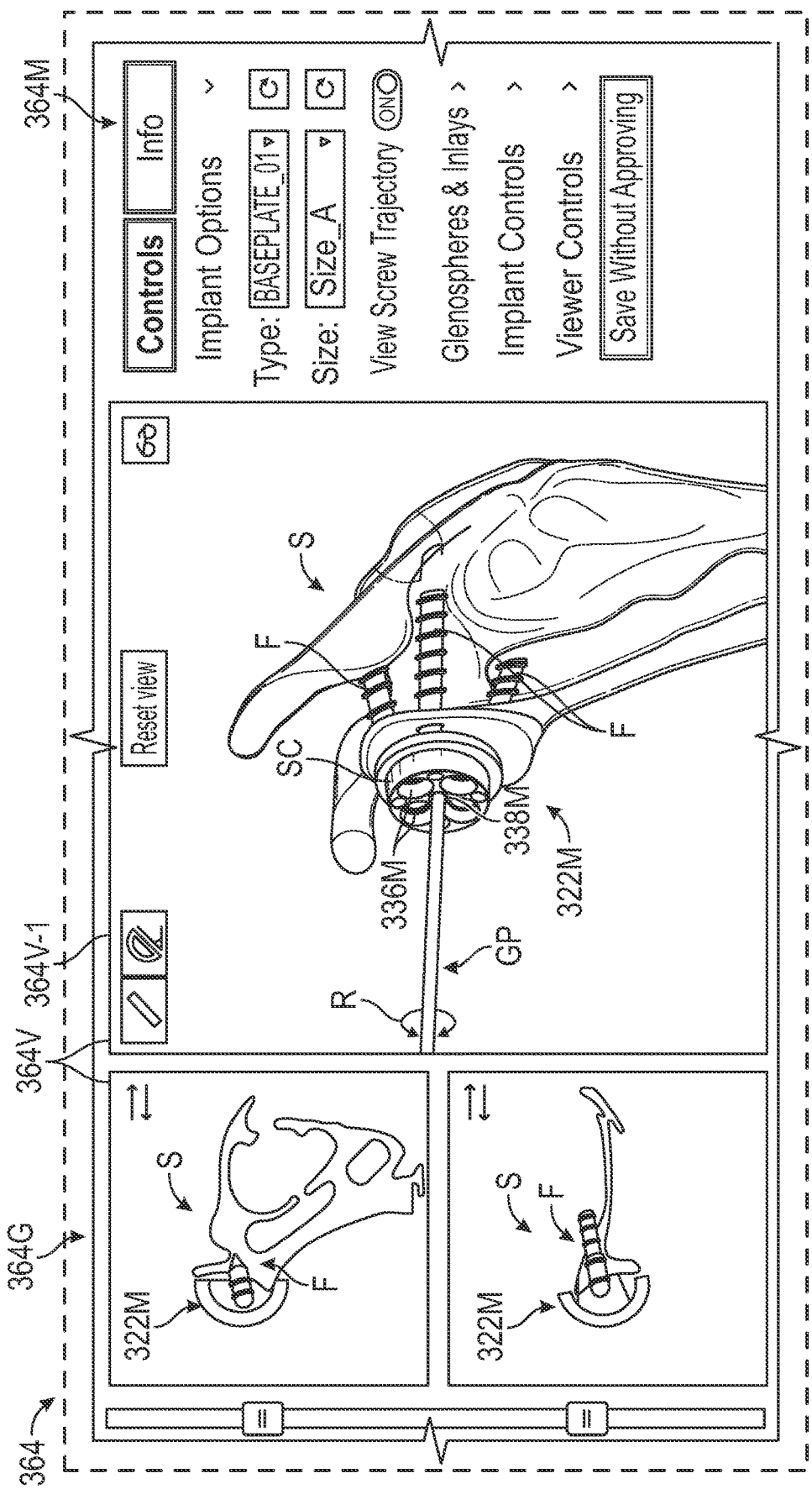
FIGS. 10-12 illustrates aspects of an implant model in an exemplary planning system.

At step 300A, a size and/or position of a baseplate of an implant may be determined. Referring to FIG. 10, with continuing reference to FIG. 9, an exemplary imaging and planning system 364 is shown. The system 364 can be implemented as one or more software instructions and can incorporate features of the Virtual Implant Positioning™ (VIP) system provided by Arthrex®, Inc., for example. One would understand how to program the system 364 with logic to implement the techniques disclosed herein.

FIGS. 10-22 illustrate various states of a model which may correspond to a physical implant. An "M" suffix is utilized for illustrative purposes to identify an aspect of a model representative of a physical element with a like reference numeral. For simplicity, the term corresponding to the related reference numeral in combination with the "M" suffix may be utilized without explicit reference to the term "model".

The system 364 can include a graphical user interface 364G having an interactive menu 364M and one or more viewing frustums (or windows) 364V. A surgeon or another operator can interact with the interface 364G to import a CT scan, MRI or other preoperative image of a surgical site S such a shoulder of the patient into the system 364. The system 364 may be operable to display one or more views of the surgical site S in the viewing frustum(s) 364V.

The surgeon can interact with menu items of the interface 364G to specify various implant options including baseplate type and/or size. The various implant options can be preset or imported in the system 364 as one or more data tables, for example.

Step 300A can include establishing a patient-specific plan for the respective surgical site S. Step 300A can include the surgeon interacting with the interface 364G to select one or more baseplate models 322M and situate the selected baseplate model 322M relative to a 3D model of the surgical site S. Each baseplate model 322M can correspond to a representation or design of a physical baseplate, including any of the baseplates disclosed herein.

For example, the surgeon may select "Baseplate_01" from the "Type" menu item and "Size_A" from the "Size" menu item. The system 364 may be operable to display in the interface 364G a corresponding model 322M of the selected baseplate and/or a model of a guide pin GP at a selected position of the surgical site S, as illustrated by the various views of FIG. 10. The selected position can be a default position (e.g., center of a glenoid face) or can correspond to a position of the guide pin GP and/or model 322M manually manipulated by the surgeon through interaction with the interface 364G, for example.

The surgeon can interact with the interface 364G to adjust or set an orientation and/or position of the model 322M of the selected baseplate and/or guide pin GP. For example, the surgeon can move the model 322M relative to a Superior/Inferior (S/I) plane and/or Anterior/Posterior (AP) plane of the glenoid. The surgeon can interact with the interface 364G to adjust or set a height or depth of the model 322M relative to a surface contour SC (see 364V-1) of the surgical site S.

The surgeon can interact with the interface 364G to position one or more fasteners F relative to the baseplate model 322M. In the viewing frustum 364V-1, four fasteners F may be situated in respective plate apertures 336M and the guide pin GP may be situated in a central aperture 338M of the model 322M. The surgeon can interact with the system 364 to rotate the model 322M in a direction R about the guide pin GP prior to positioning the fasteners F to set a position of the model 322M relative to the surgical site S.

The surgeon can interact with one or more menu items of the interface 364G to approve the settings, such as by selection of an "Approve" button.

Figure 11:
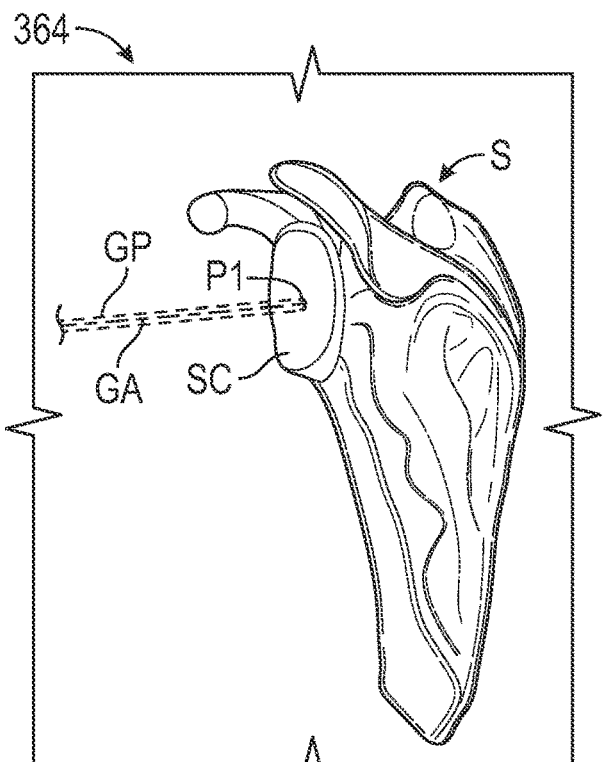

Referring to FIG. 11, with continuing reference to FIGS. 9-10, at step 300B the surgeon can interact with the system 364 to set or define a trajectory of the guide pin GP (shown in dashed lines for illustrative purposes). The guide pin GP extends along a guide pin axis GA which may intersect the surface contour SC of the surgical site S at a point P1.

Figure 12:
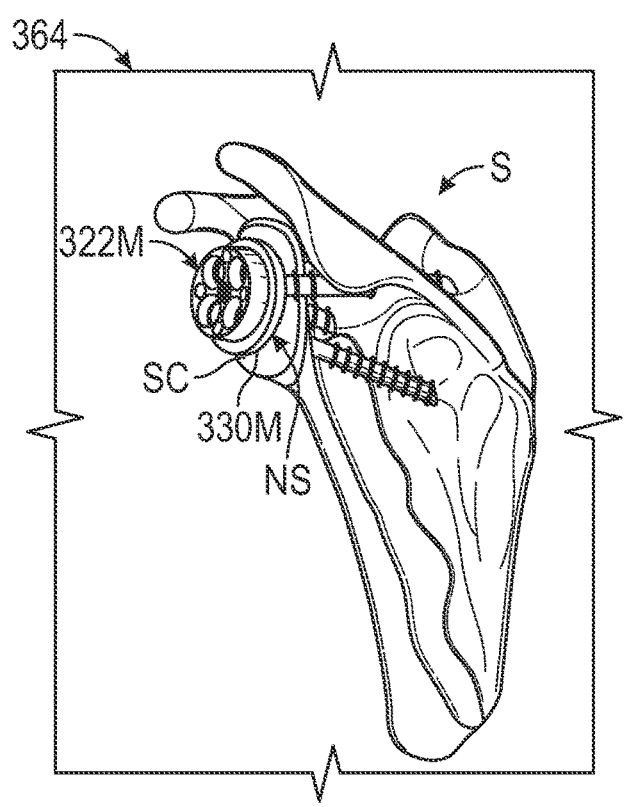

Referring to FIG. 12, with continuing reference to FIGS. 9-10, at step 300C a negative space NS may be defined between a rear face 330M of the model 322M and the surface contour SC. The rear face 330M may be offset by a selected distance from the surface contour SC.

Figure 13:
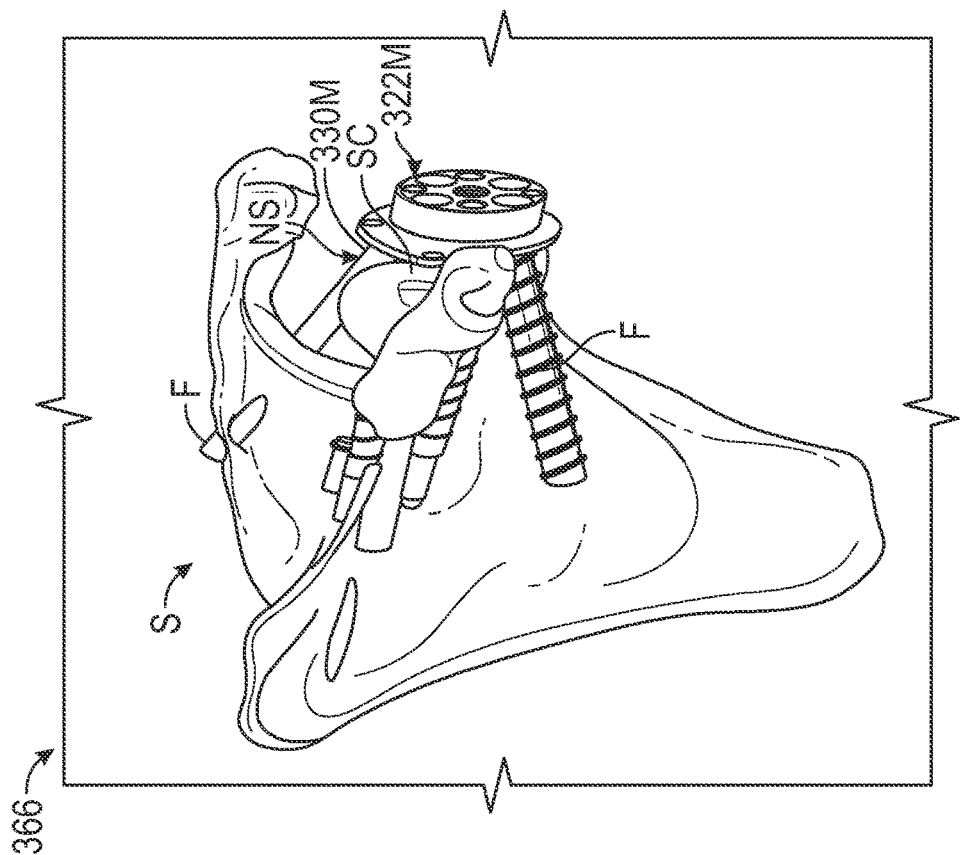

Referring to FIG. 13, with continuing reference to FIGS. 9-10, at step 300D the model 322M may be positioned in at least one computer aided design (CAD) tool 366 to match the trajectory of the guide pin GP, negative space NS and offset of the rear face 330M of the model 322M which may be determined at steps 300B, 300C. The tool(s) 366 can be a separate system or can be incorporated into the system 364.

Figure 14:
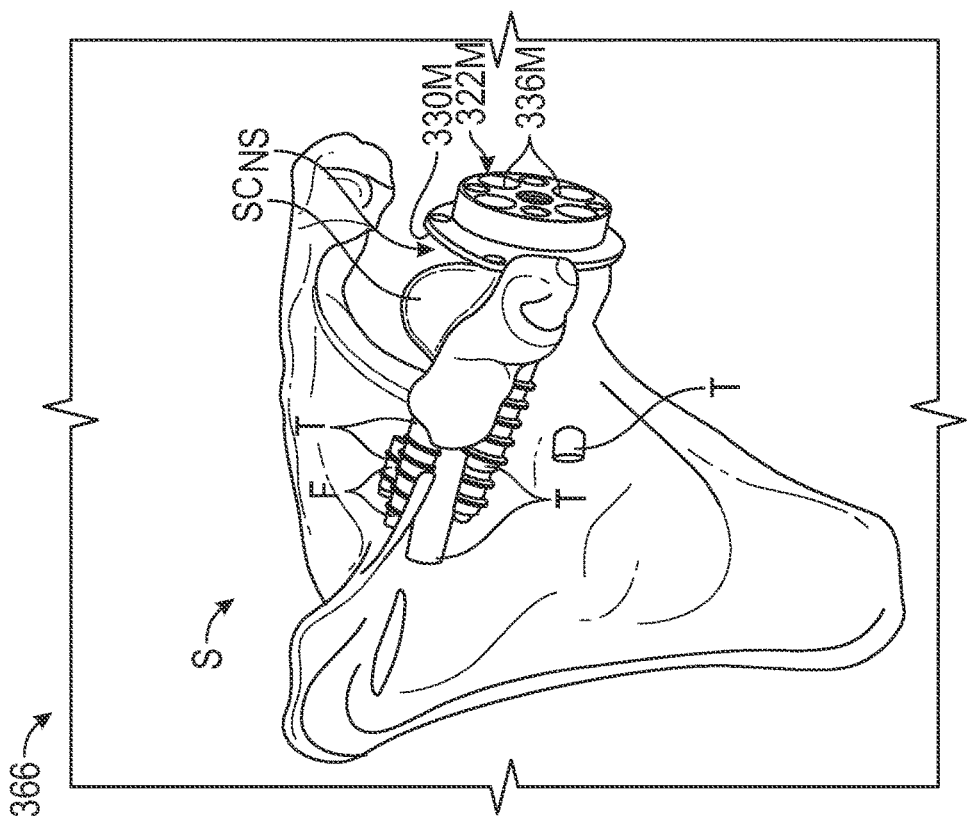
FIGS. 13-22 illustrates aspects of an implant model in an exemplary tool.
Figure 15:
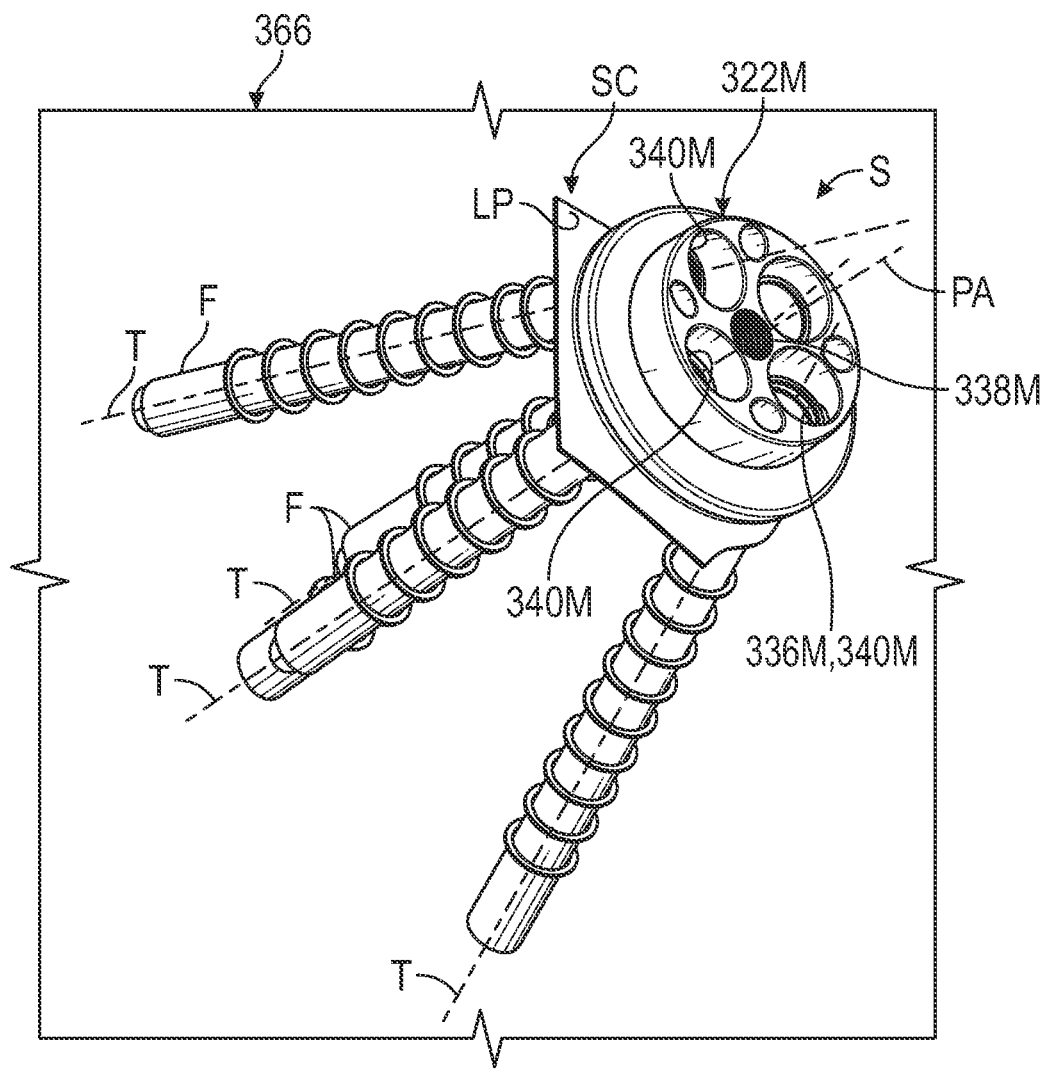

Referring to FIG. 14, with continuing reference to FIG. 9-10, at step 300E the surgeon or operator can interact with the system 364 and/or tool 366 to set or reposition the trajectories T of the respective fasteners F which may increase bone thread contact and fixation (e.g., bone screw purchase) and/or a length of the fasteners F based on bone quality and bone stock along the surgical site S, for example. The trajectories T can be utilized to set or define a trajectory of an aperture axis PA of the respective plate aperture 336M, as illustrated in FIG. 15. Step 300E can be utilized to revise an initial patient-specific plan established at step 300A.

Referring to FIG. 15, with continuing reference to FIGS. 9 and 14, at step 300F the defined or selected characteristics of the model 322M (e.g., as modified from step 300A) including the trajectories T and a localized portion LP of the surface contour SC may be stored in the system 364 for subsequent design operation(s) such as mesh or solid definition. Localization of the surface contour SC can simplify subsequent computations and other design operations.

Figure 16:
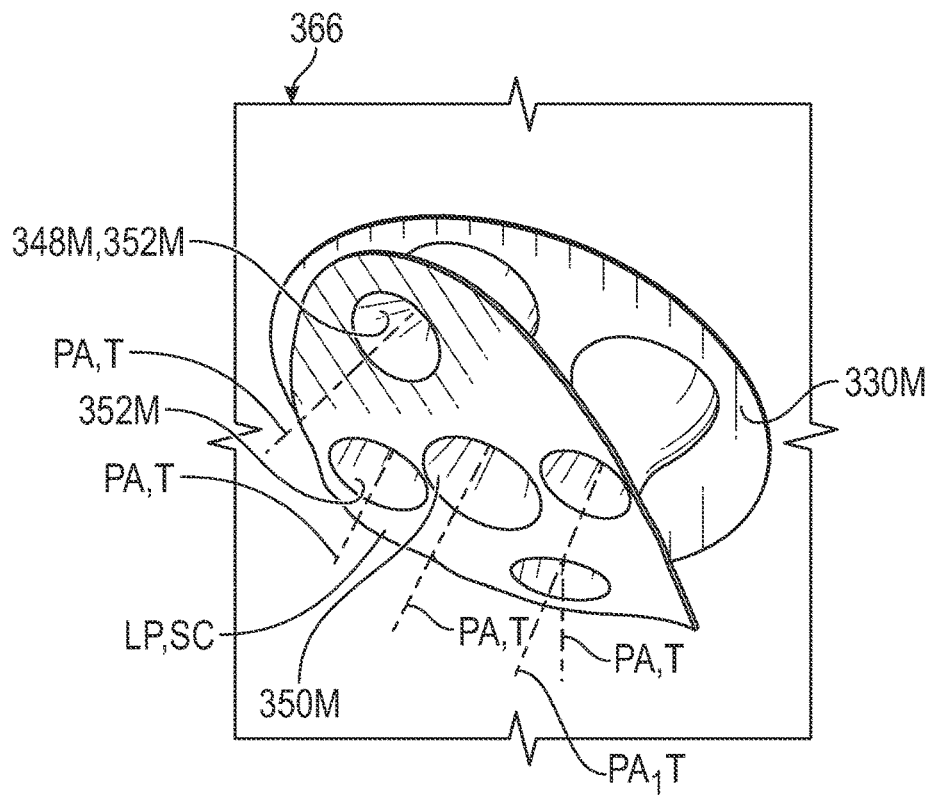
Figure 17:
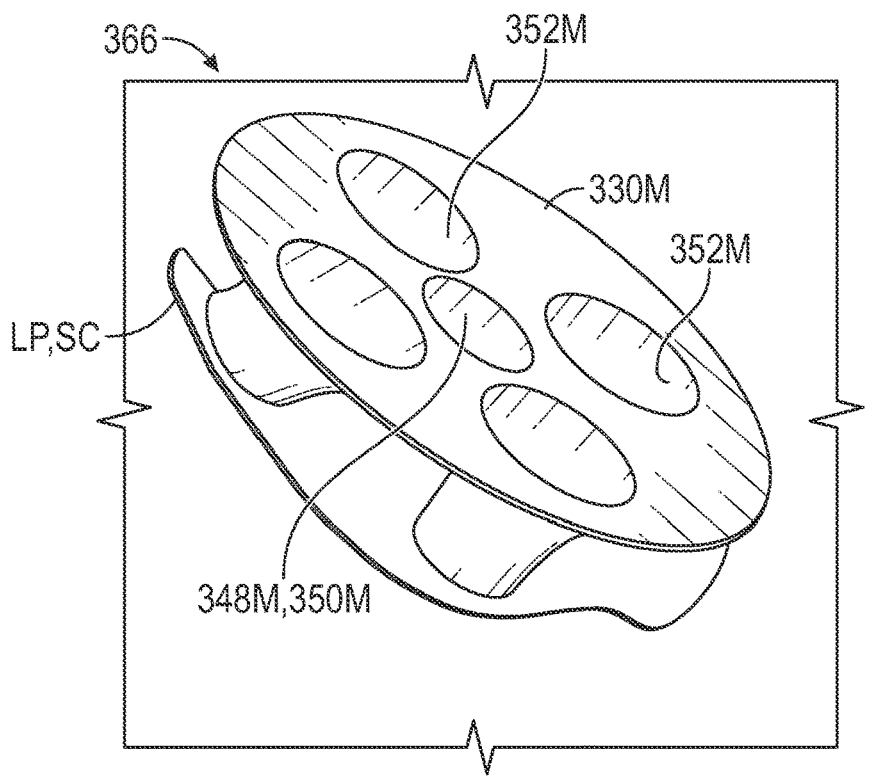

Referring to FIGS. 16-17, with continuing reference to FIG. 9, at step 300G a surface contour of the rear face 330M and an adjacent region of the localized portion LP of the surface contour SC together with the defined trajectories T of the fasteners F and the trajectories of the aperture axes PA of the plate apertures 336M (FIG. 16) may be isolated in the tool 366.

Figure 18:
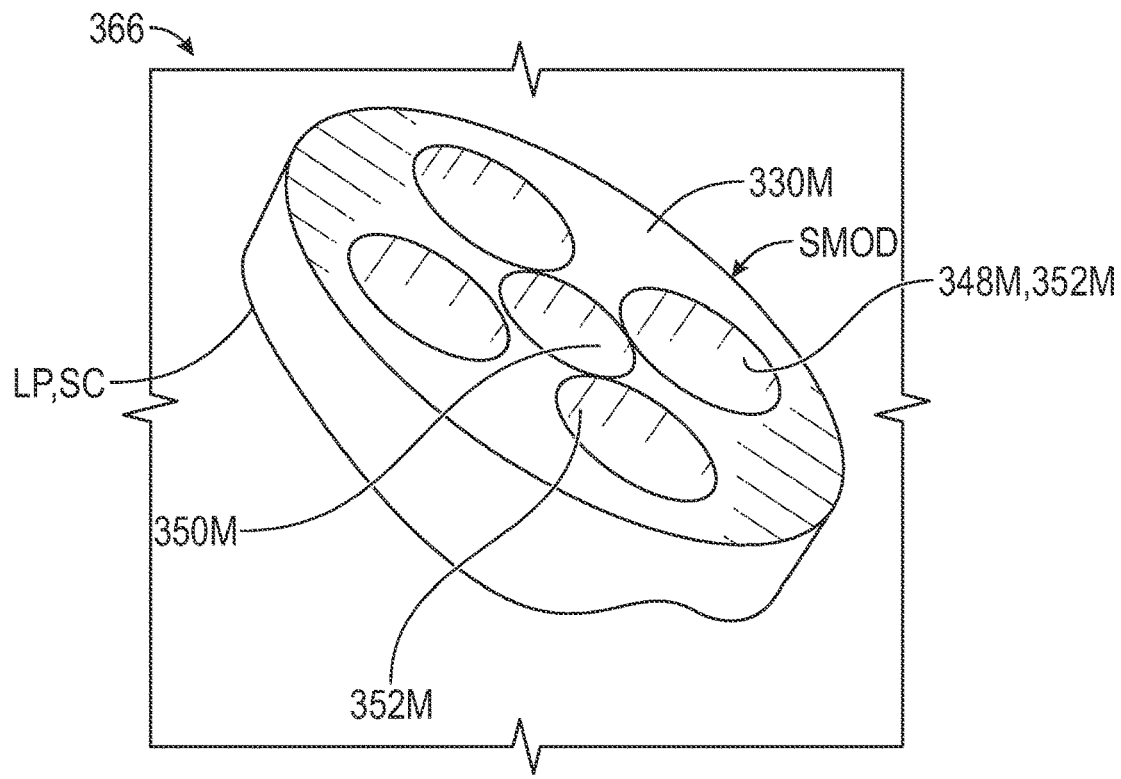
Figure 19:
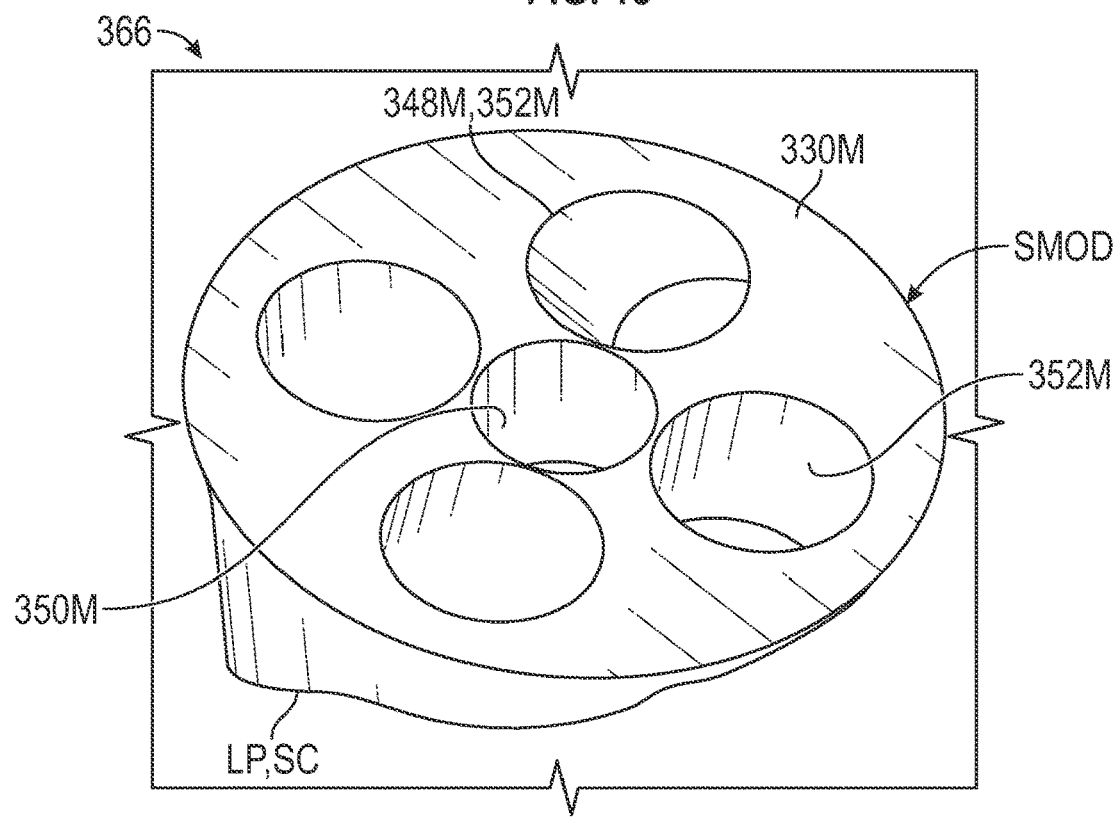

Referring to FIGS. 18-19, with continuing reference to FIG. 9, at step 300H a solid model SMOD may be created or generated from the surfaces of the rear face 330M and the localized portion LP of the surface contour SC. One or more void spaces (or aperture voids) 348M may be defined along the trajectory of the respective aperture axes PA and/or along the trajectory T of the respective fasteners F (see FIG. 16).

The void spaces 348M may correspond to or are otherwise associated with a respective augment aperture dimensioned to receive a respective fastener F and/or guide pin GP (see, e.g., augment apertures 48 of FIG. 2). For example, a diameter of the void space 348M may be substantially equal to or may be greater than a diameter of a respective one of the fasteners F and/or augment apertures.

Figure 20:
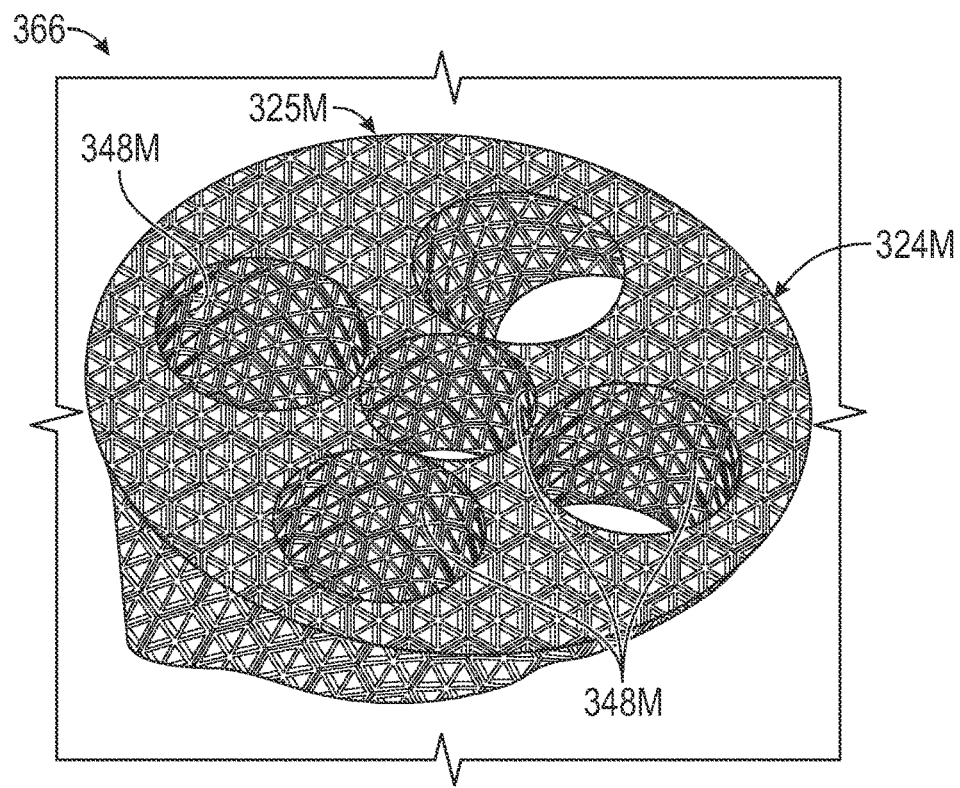

Referring to FIG. 20, with continuing reference to FIGS. 9 and 18-19, at step 300I an augment model (or volume) 324M may be defined or generated from the solid model SMOD. The augment model 324M may be associated with a respective baseplate selected during step 300A.

The augment model 324M may be defined or dimensioned to extend between the rear face 330M of the respective baseplate 322M and a predefined surface contour SC of a bone surface according to step 300G. A profile of the predefined surface contour SC may be determined prior to defining the augment model 324M at step 300I. The predefined surface contour SC can be a patient-specific surface contour of a glenoid face, for example.

The augment model 324M may be substantially solid or porous. The augment model 324M may include an augment body 342M that is substantially solid, as illustrated by the augment model 324M-1 of FIG. 27B. The augment model 324M may be a porous scaffold including an interconnected network of branches and nodes extending throughout a volume of the model 324M, as illustrated in FIG. 20 and by the augment models 324M-2 to 324M-6 of FIG. 27B.

One or more void spaces 348M in the augment model 324M may be defined along the trajectory T of the respective fasteners F and/or the trajectory of the aperture axis PA of the respective plate apertures 336M according to steps 300E, 300F (see FIGS. 15-16). Respective augment apertures 348 may be defined according to the void spaces 348M such that the augment apertures 348 may be matched with respective plate apertures 336, as illustrated by the implants 320 of FIG. 27B and by the apertures 36, 48 of the implant 20 of FIG. 2.

Figure 21:
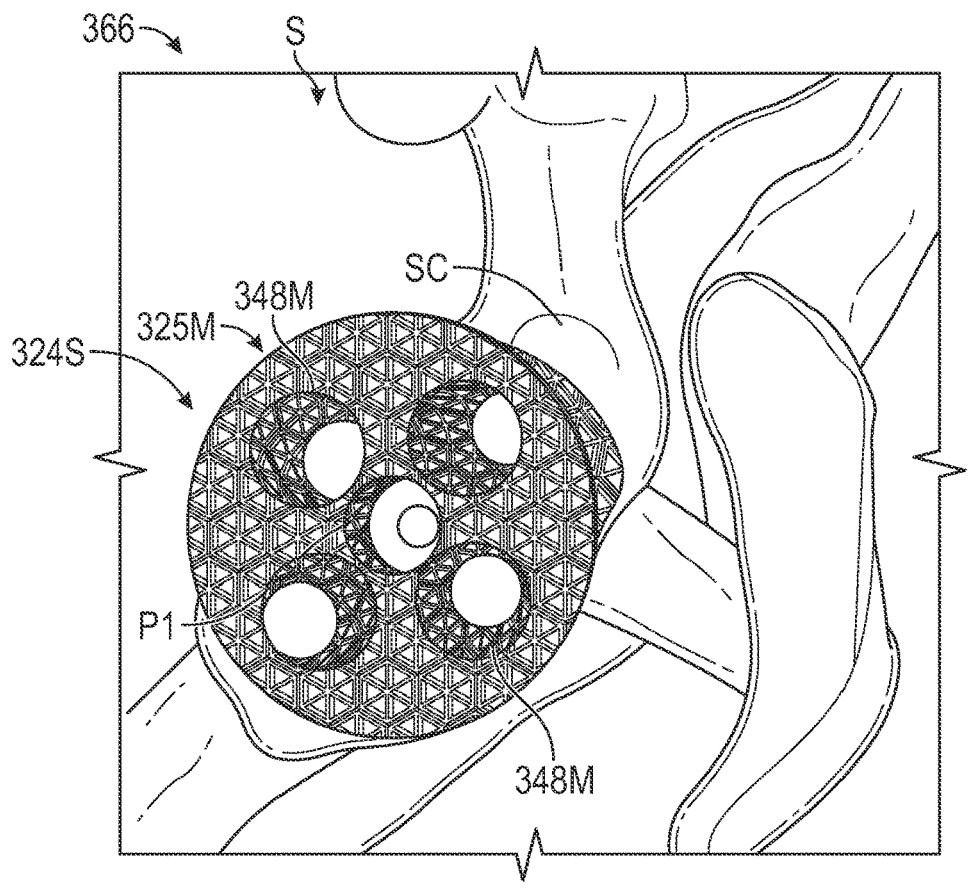

Referring to FIG. 21, with continuing reference to FIGS. 9-10 and 20, at step 300J the augment model 324M established at step 300I may be positioned on the surface contour SC of a model of the surgical site S. The augment model 324M can be positioned relative to the point P1 associated with a predefined position and orientation of the guide pin GP at step 300B (see FIG. 11). Step 300J can include comparing the augment model 324M to an anatomy of the patient, including validating that a geometry of the designed augment model 324M matches or conforms to a geometry of the surface contour SC of the surgical site S.

Figure 22:
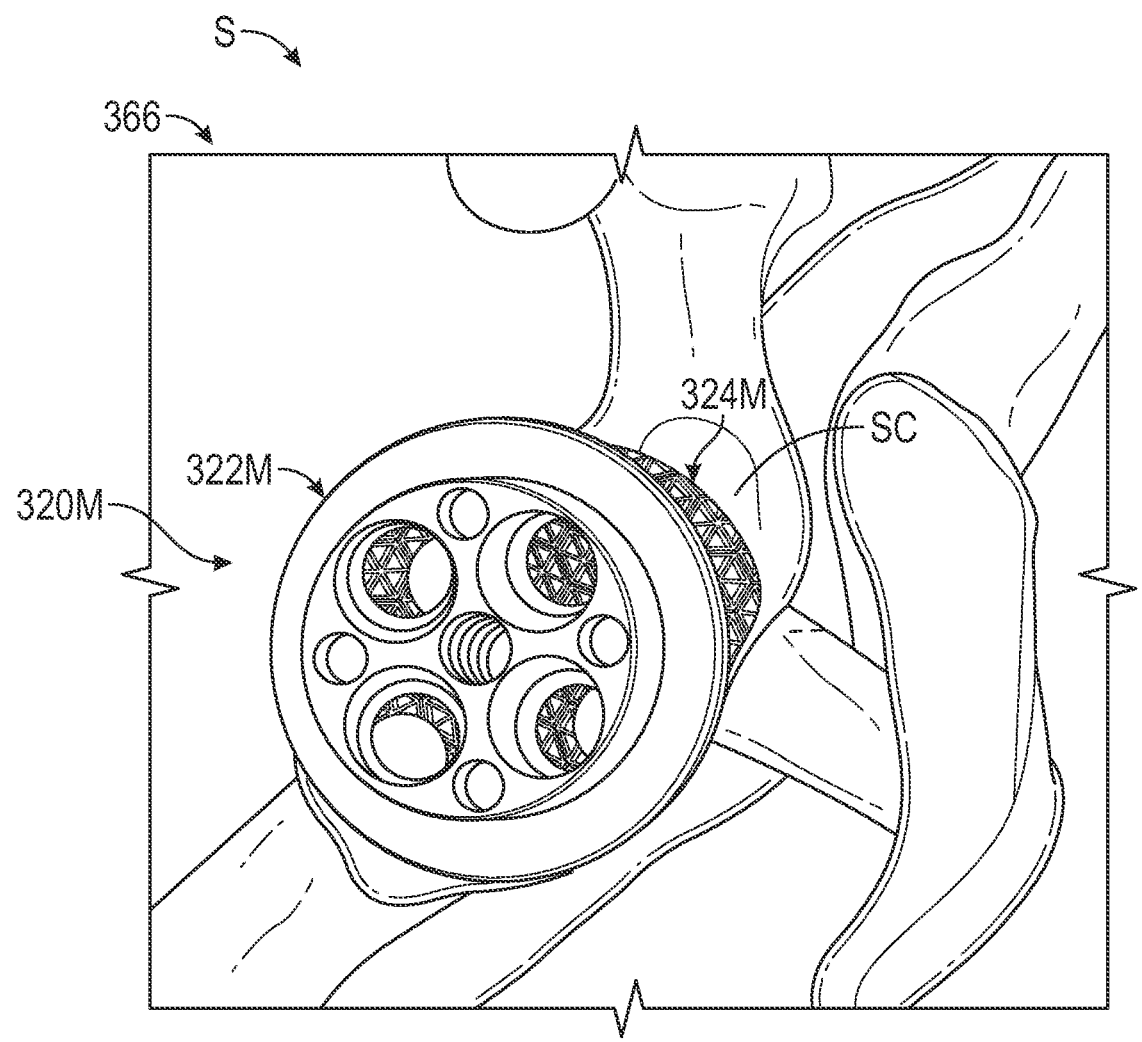

Referring to FIG. 22, with continuing reference to FIGS. 9-10 and 21, at step 300K the baseplate model 322M may be positioned on, and relative to, the augment model 324M to complete a design definition of the respective implant 320M.

Figure 23:
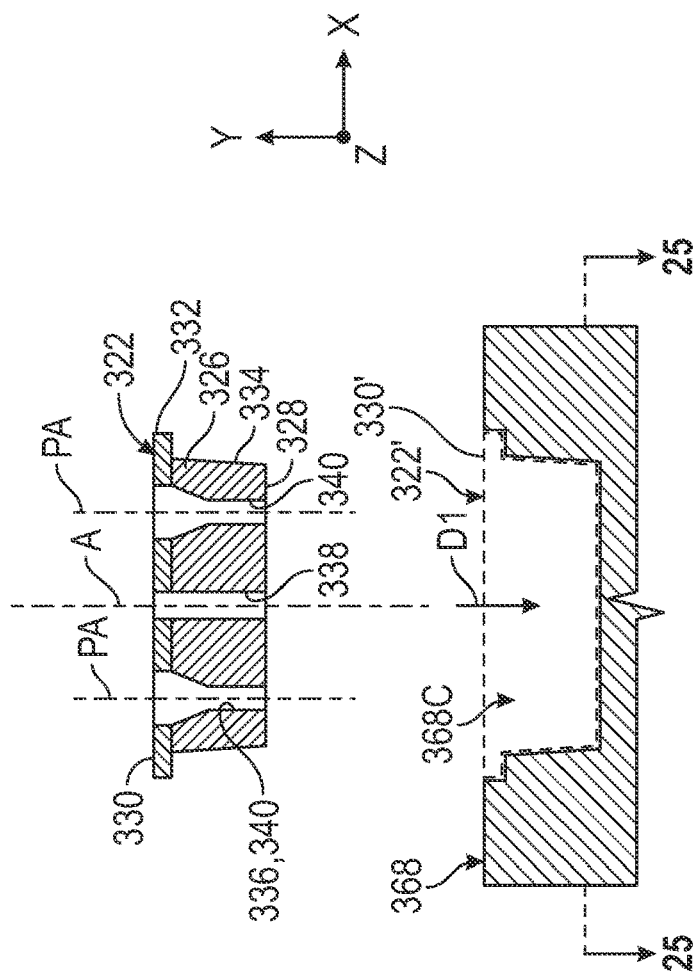
FIGS. 23-24 illustrate exemplary baseplates positioned in a fixture.
Figure 24:
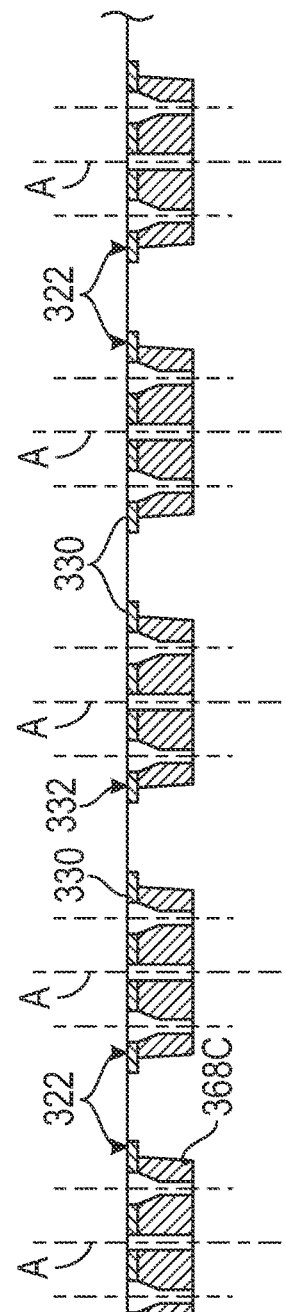

Various techniques can be used to form the implants according to the design definition. Referring to FIG. 23-24, with continuing reference to FIG. 9, at step 300L at least one baseplate 322 may be positioned relative to a fixture (or build plate) 368 such that a rear face 330 of the baseplate 322 is exposed (also shown at 322' in dashed lines in FIG. 23 for illustrative purposes). Each baseplate 322 can be a pre-manufactured and pre-inspected standardized implant blank. The fixture 368 can be a metallic component including cavities (or pockets) 368C machined or otherwise formed in a face of the fixture 368.

Figure 27A:
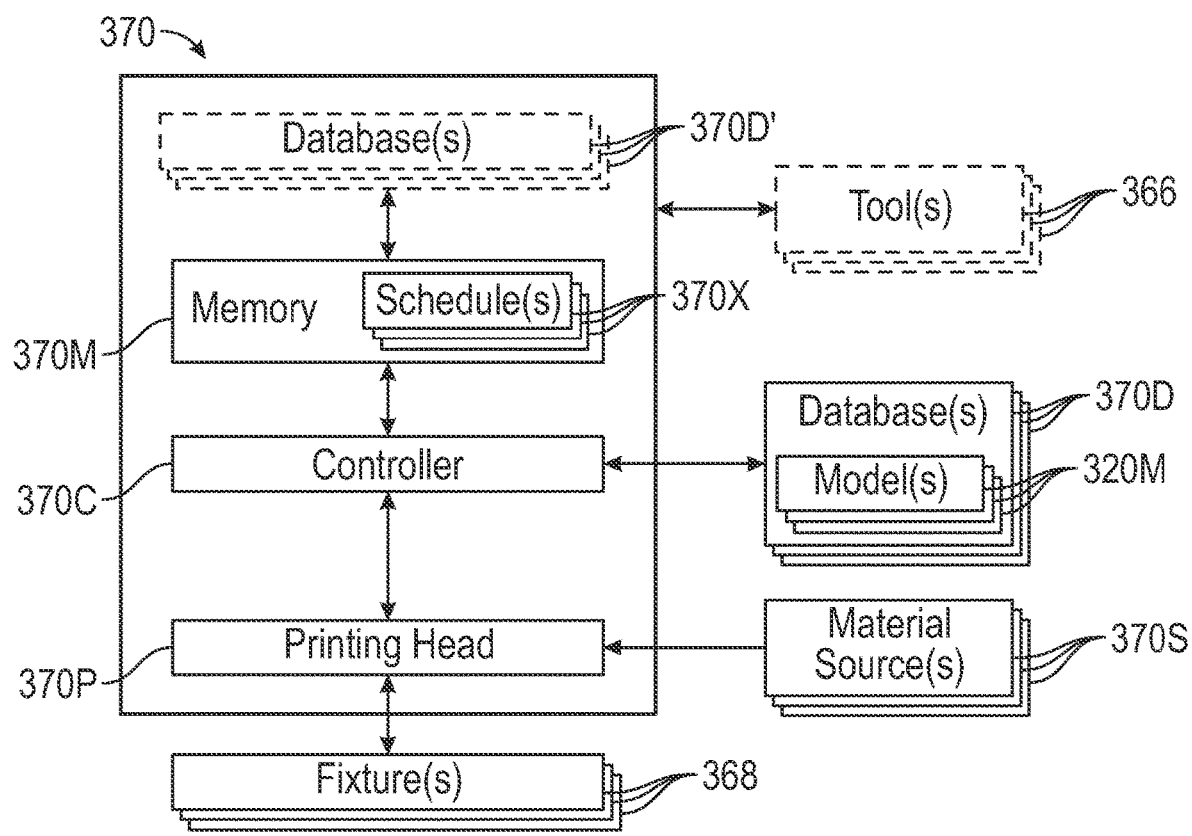
FIGS. 27A-27B illustrates an exemplary additive manufacturing system which may be utilized to form one or more implants.
Figure 27B:
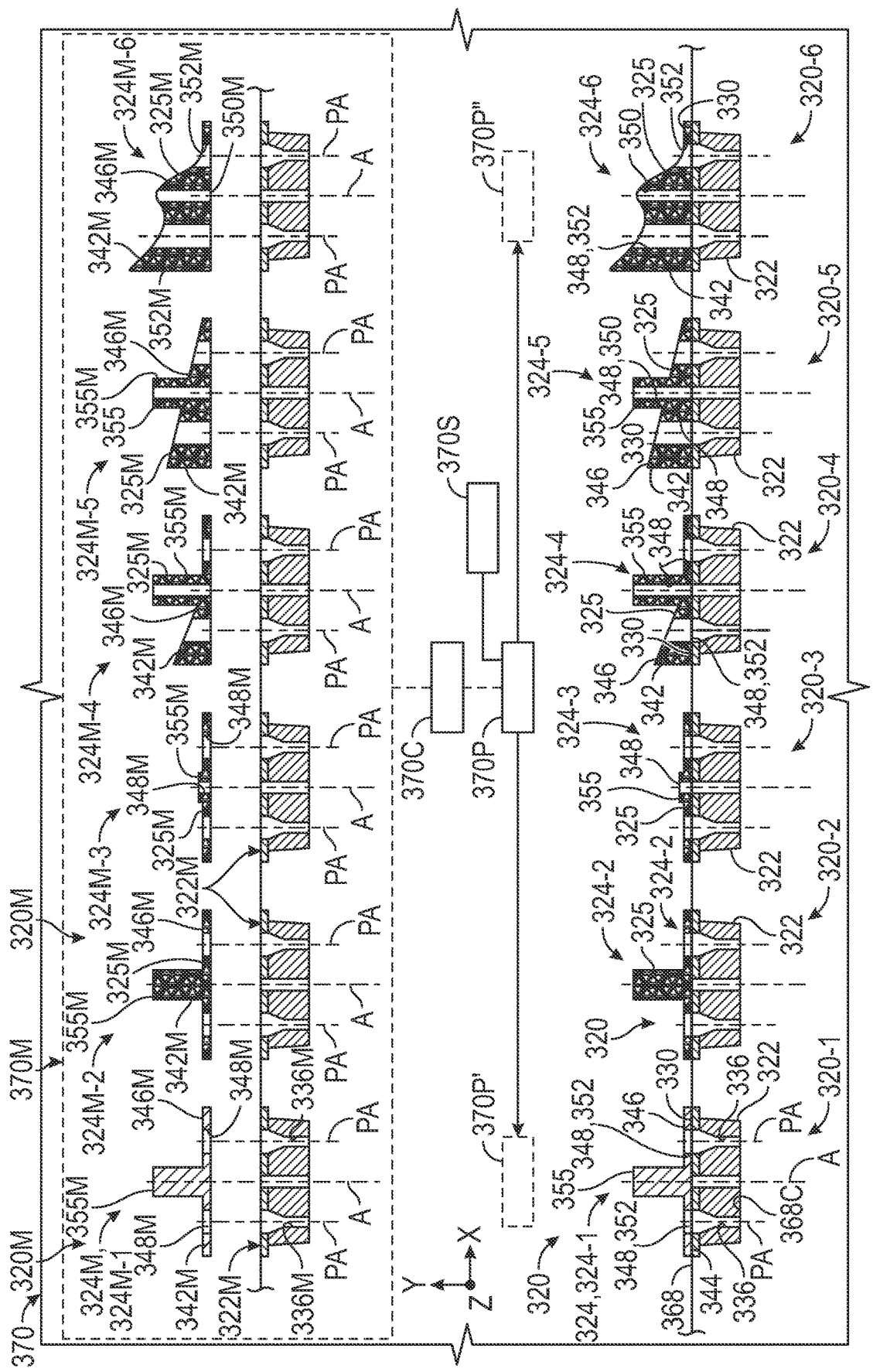

The fixture 368 can be utilized with or incorporated into a bed of an additive manufacturing or three-dimensional (3D) printing machine or system, such as the machine or system 370 of FIGS. 27A-27B. A set of baseplates 322 can be presented together in the fixture 368 for forming the respective augments 324. Additive manufacturing includes a process of forming a 3D object from a digital file such as a computer-aided design (CAD) model typically by addition of one or more successive layers of material. However, additive manufacturing to form portions of an implant utilizing the techniques disclosed herein is not known.

Step 300L can include moving the baseplate 322 with the front face 328 in a downward position in a direction D1 into a respective cavity 368C of the fixture 368. The cavity 368C can be dimensioned to conform to or otherwise complement a geometry of the respective baseplate 322. The rear face 330 of the baseplate 322 can have a substantially planar geometry, as illustrated in FIGS. 23-34. Step 300L can include positioning a set of baseplates 322 at respective locations along the fixture 368, as illustrated by FIG. 24.

Figure 25:
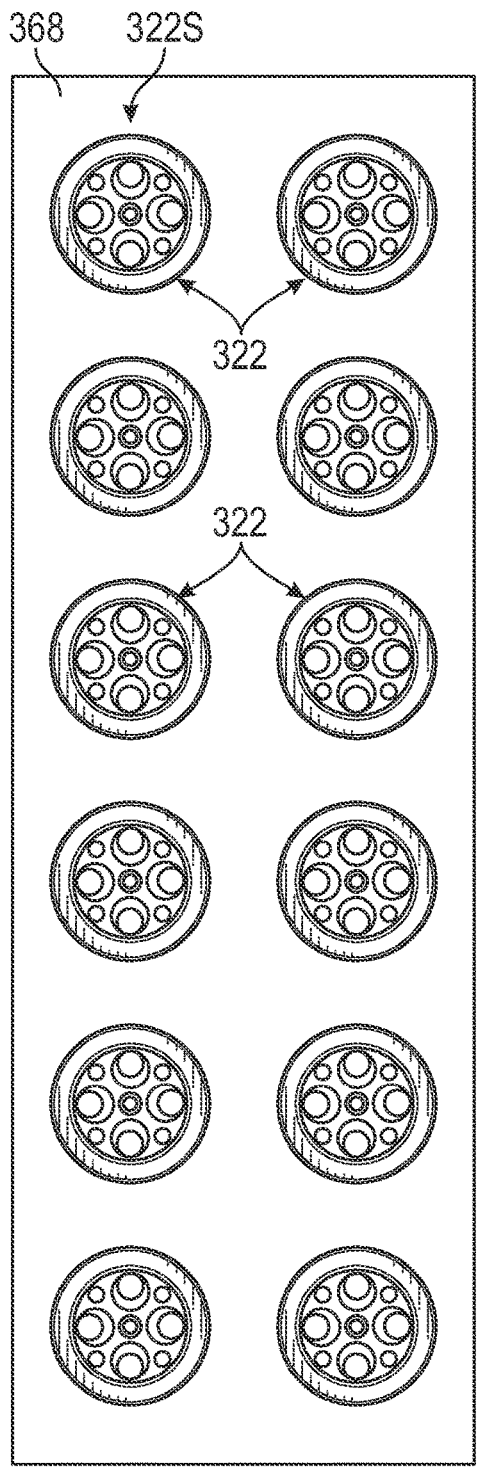
FIGS. 25-26 illustrate sets of exemplary baseplates positioned in respective fixtures.

FIGS. 24-25 illustrate a set 322S of the baseplates 322 may be positioned in rows at respective locations along the fixture 368. It should be appreciated that any number of baseplates 322 can be positioned in the fixture 368 in view of the teachings disclosed herein. A geometry of the baseplates 322 positioned in the fixture 368 can be the same or can differ. Each baseplate 322 in the set 322S may have the same geometry, as illustrated in FIG. 25. The geometry of the baseplates 322 may correspond to the baseplate 22 of FIGS. 1-4, for example.

Figure 26:
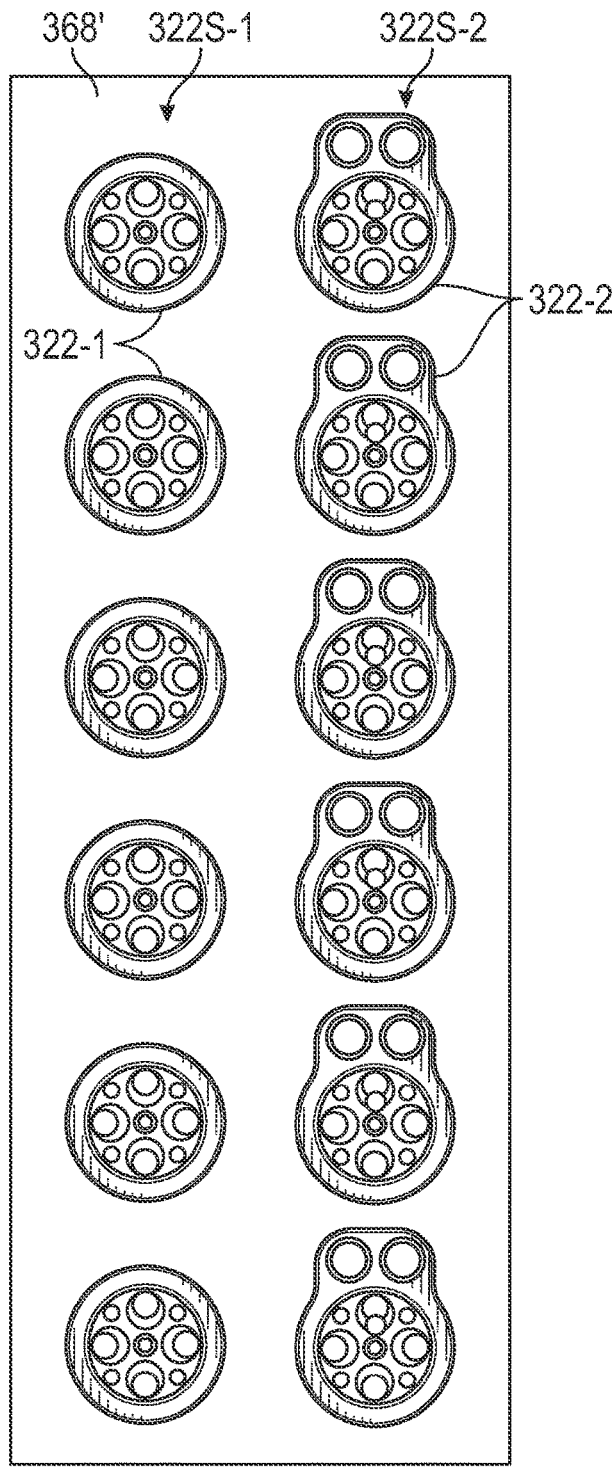

In FIG. 26, a first set 322S-1 of baseplates 322-1 and a second set 322S-2 of baseplates 322-2 may be positioned at respective locations along the fixture 368'. A geometry of the first set 322S-1 of baseplates 322-1 may differ from a geometry of the second set 322S-2 of baseplates 322-2. The geometry of the baseplates 322-1 may correspond to the baseplate 22 of FIGS. 1-4, and the geometry of the baseplates 322-2 may correspond to the baseplate 122 of FIGS. 5-6, for example.

Referring to FIGS. 27A-27B, with continuing reference to FIGS. 9 and 24, the system 370 may include at least a controller 370C coupled to at least one printing head 370P. The printing head 370P may be coupled to one or more material sources 370S that each may supply a respective amount of material in operation, including any of the materials disclosed herein. The materials supplied by the material sources 370S may be the same or may differ.

The controller 370C may include one or more computing devices, each of which may have one or more of a computer processor, memory, storage means, network device and input and/or output devices and/or interfaces. The memory may, for example, include UVPROM, EEPROM, FLASH, RAM, ROM, DVD, CD, a hard drive, or other computer readable medium which may store data and/or the algorithms corresponding to the various functions of this disclosure. The controller 370C may interface with, or be integrated into, the system 364 and/or one or more CAD tools 366.

The system 370 may be connected to one or more databases 370D, as illustrated in FIG. 27A. Each database 370D may be external to the system 370 and/or internal to the system 370 (shown in dashed lines at 370D' for illustrative purposes). Each database 370D may be configured to store one or more implant models 320M in a predefined data structure or format. Each implant model 320M stored in the database 370D includes a respective data set defining a geometry of a physical implant including a baseplate and augment. The database 370D can be configured to store implant models 320M having patient-specific and/or standardized baseplate and augment geometries, including any of the implants disclosed herein. The controller 370C is operable to access each database 370D and store the implant model(s) 320M and related information in the memory 370M.

The controller 370C may be operable to load a coordinate set associated with one or more implant models 320M from the memory 370M. Each implant model 320M can include a respective baseplate and augment models 322M, 324M. The coordinate set(s) can be normalized or defined relative to one or more reference points associated with the fixture 368. The controller 370C is operable to execute one or more predefined schedules 370X (FIG. 27A) which may be stored in the memory 370M. Each predefined schedule 370X is defined with respect to a geometry of the baseplate model 322M of the baseplate(s) 322 at the respective position(s) in the fixture 368 and the augment model 324M of the augment(s) 324 to be formed on the respective baseplate(s) 322.

The implant models 320M can be the same or can differ. For example, step 300I can occur such that the augment model (or volume) 324M associated with a baseplate 322 of the set 322S of baseplates 322 differs from the augment model 324M associated with another baseplate 322M of the set of baseplates 322M, as illustrated by the augment models 324M-1 to 324M-6 of FIG. 27B.

FIG. 27B illustrates various exemplary geometries of the augment models 324M (indicated at 324M-1 to 324M-6). It should be understood that the geometries of FIG. 27B are exemplary and other geometries can be utilized in accordance with the teachings disclosed herein.

Augment model 324M-1 may be substantially solid and may include an anchoring stem or post 355M which may extend outwardly from a rear face 346M of an augment body 342M. The anchoring stem 355M can be dimensioned to extend along a central axis A of the baseplate model 322M. The anchoring stem 355M may be offset from the central axis A. The anchoring stem 355M can have a substantially cylindrically geometry and may be dimensioned for insertion in a bone or glenoid hole which may be formed in a glenoid to secure the respective baseplate 322, for example. The rear face 346M may have a substantially planar geometry. Augment model 324M-2 may include a porous scaffold 325M that may establish an augment body 342M, surfaces of a rear face 346M and/or anchoring stem 355M.

Augment model 324M-3 has an anchoring stem or post 355M which may include an augment aperture 348M dimensioned to at least partially receive a fastener and/or guide pin.

Augment model 324M-4 includes an augment body 342M which may have a partially wedge-shaped geometry and may include an anchoring stem 355M which may extend outwardly from a rear face 346M of the augment 324M. Augment model 324M-5 includes an augment body 342M which may have a substantially full wedge-shaped geometry and may include an anchoring stem 355M which may extend outwardly from a rear face 346M of the augment 324M.

Augment model 324M-6 includes an augment body 342M having a rear face 346M which may be dimensioned to match or substantially correspond to a patient-specific surface contour of a bone surface, such as a glenoid face. The augment body 342M can include a central augment aperture 350M and/or one or more peripheral augment apertures 352M. The augment model 324M-6 may correspond to a geometry of the augment 24 of FIGS. 1-4. Augment model 324M-6 can includes a porous scaffold 325M that may establish an augment body 342M, surfaces of the rear face 346M and/or anchoring stem 355M.

The controller 370C can be programmed with logic to command the printing head 370P to move to various positions or locations relative to the fixture 368 (illustrated in dashed lines at 370P', 370P'') and cause the printing head 370P to print or deposit material along the baseplates 322 according to each of the implant models 320M specified in the predefined schedule 370X. Each baseplate 322 can serve as a substrate for formation of a respective augment 322.

At step 300M, the controller 370M may cause the printing head 370P to print or otherwise form at least one augment 324 on the rear face 330 of a respective baseplate 322 according to the respective augment model (or volume) 324M to form an implant 320. Step 300M can include moving the printing head 370P across the rear face 330 of each respective baseplate 322. Step 300L may include fixing a position of each fixture 368 relative to the system 370 such that the fixture 368 is constrained in motion (e.g., in the x, y and/or z axes, see FIGS. 23 and 27B) relative to the system 370 during formation of the augment(s) 324 at step 300M. An augment body 342 may be established along a rear face 330 of the respective baseplate 322.

The augment 324 may correspond to the augment model 324M defined at step 300I, for example. The augment models (or volumes) 324M may be predefined or predetermined prior to step 326. Step 300M can include establishing an anchoring stem 355 that extends outwardly from the augment body 342, as illustrated by implant 320-1.

Step 300M can include printing any of the materials disclosed herein to establish the respective augments 324. Step 300M may occur such that a first material of the baseplate 322 differs from a second material of the respective augment 324, such as different porosities, including any of the porosities disclosed herein. Step 300M can include forming the augment 324 to be substantially solid, as illustrated by the augment 324-1 of FIG. 27B, and/or can include forming the augment 324 to establish a porous scaffold, as illustrated by the scaffolds 325 of the augments 324-2 to 324-6 of FIG. 27B and by a scaffold 25 of the augment 24 of FIGS. 1-1A, for example.

Step 300M may occur such that at least one augment aperture 348 is established in the augment 324 according to the void space(s) 348M and along the trajectory of each respective aperture axis PA defined at step 300I (see FIGS. 18-19). For example, the implant 320-1 may include a plurality of plate apertures 336 distributed along the rear face 330 of the baseplate 322, and may include a plurality of augment apertures 348 aligned with respective ones of the plate apertures 336. The augment apertures 348 may include peripheral augment apertures 352 which may be circumferentially distributed about a longitudinal axis LA of the anchoring stem 355.

Step 300M can occur such that at least a portion of the rear face 346 of the augment 324 is transverse to the rear face 330 of the baseplate 322, with one or more augment apertures 348 extending between the portion of the rear face 330 and the front face 344 of the augment 324, as illustrated by implants 320-4 to 320-6. The rear face 346 of the augment 324 may be dimensioned to contact bone, and the front face 344 may be disposed along the rear face 330 of the baseplate 322.

The method 300 can be utilized to form a set of implants 320. Various augment and aperture profiles or geometries can be established to correspond to or approximate a variety of different surface profiles and void geometries that may be encountered by the surgeon in preparation of surgery.

The steps of the method 300 including defining the augment model 324M and/or printing the respective augment 324 can be repeated for a set of baseplates 322 according to the predefined schedule 370X, such as the baseplates 322 corresponding to the implants 320-2 to 320-6, for example. Each augment model 324M corresponding to the set of baseplates 322 and the respective predefined schedule 370X can be defined prior to step 300M.

The steps of the method 300 including defining the augment model 324M and/or printing the respective augment 324 can be repeated for a second set of baseplates 322, and step 300L can include positioning the second set of baseplates 322 at respective locations along the fixture 368, as illustrated by the first and second sets 322S-1, 322S-2 of baseplates 322 of FIG. 26. Step 300I can occur such that the augment model (or volume) 324M is common to each augment 324 corresponding to the second set 322S-2 of baseplates 322, for example. Each implant 320 can be removed from the fixture 368 subsequent to step 300M for implanting in a respective patient.

The surgeon can be provided with a set of orthopedic implants in a kit for arthroplasty, including any of the implants disclosed herein. The kit can include a set of baseplates having any of the baseplates, augment geometries and aperture arrangements disclosed herein. For example, the kit can include first and second sets of baseplates such as the baseplates 322 of the sets 322S-1, 322S-2 of FIGS. 25-26. The predefined augment model (or volume) 324M associated with the baseplates 322 in the first and/or second sets 322S-1, 322S-2 of baseplates 322 can differ or can be common with other baseplates 322 in the respective set 322S-1/322S-2. The predefined augment model 324M can correspond to a respective patient-specific surface contour such that at least some augments 324 in the set of implants 320 differ in geometry.

The kit can include fasteners that may be received in respective peripheral apertures to secure the respective baseplate to the surgical site. The kit can include glenospheres of various sizes and geometries for securing to a selected implant.

Figure 28:
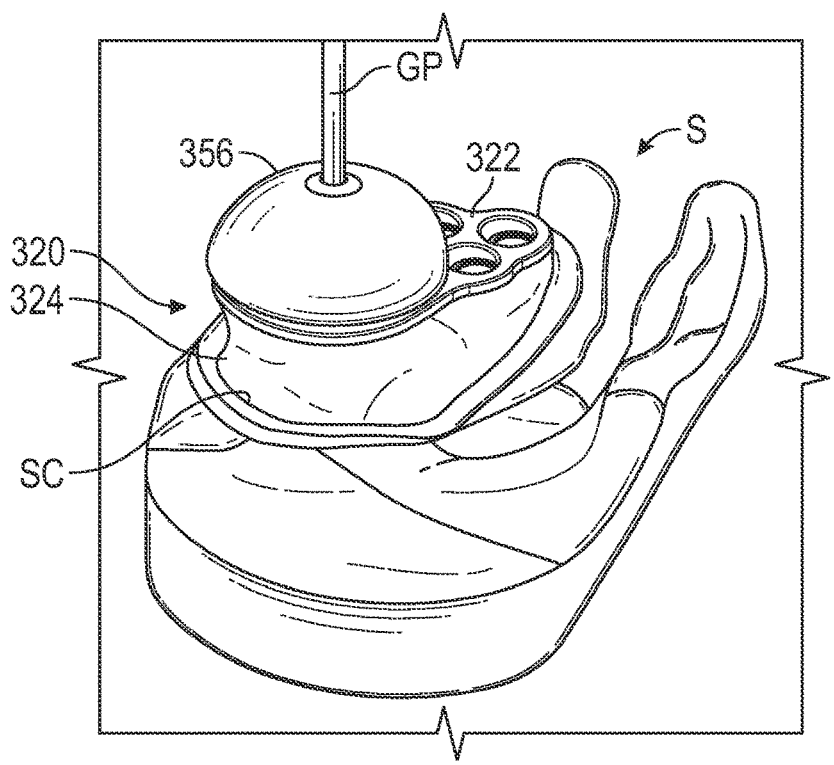
FIG. 28 illustrates an exemplary implant positioned relative to a physical model of a surgical site.

Referring to FIG. 28, with continuing reference to FIGS. 9 and 27B, at step 300N each implant 320 formed at step 300M can be inspected for conformity to the respective augment model 324M (FIG. 27B). The implant 320 may be positioned relative to a physical model of the surgical site S. Various inspection techniques can be utilized, such as optically inspecting the printed augment 324 with a point camera and digitally comparing the printed augment 324 with the CAD design of the respective augment model 324M to ensure accuracy of manufacture. The implant 320 can be positioned relative to a position and trajectory of the guide pin GP determined at step 300B (see FIG. 11), for example.

Figure 29:
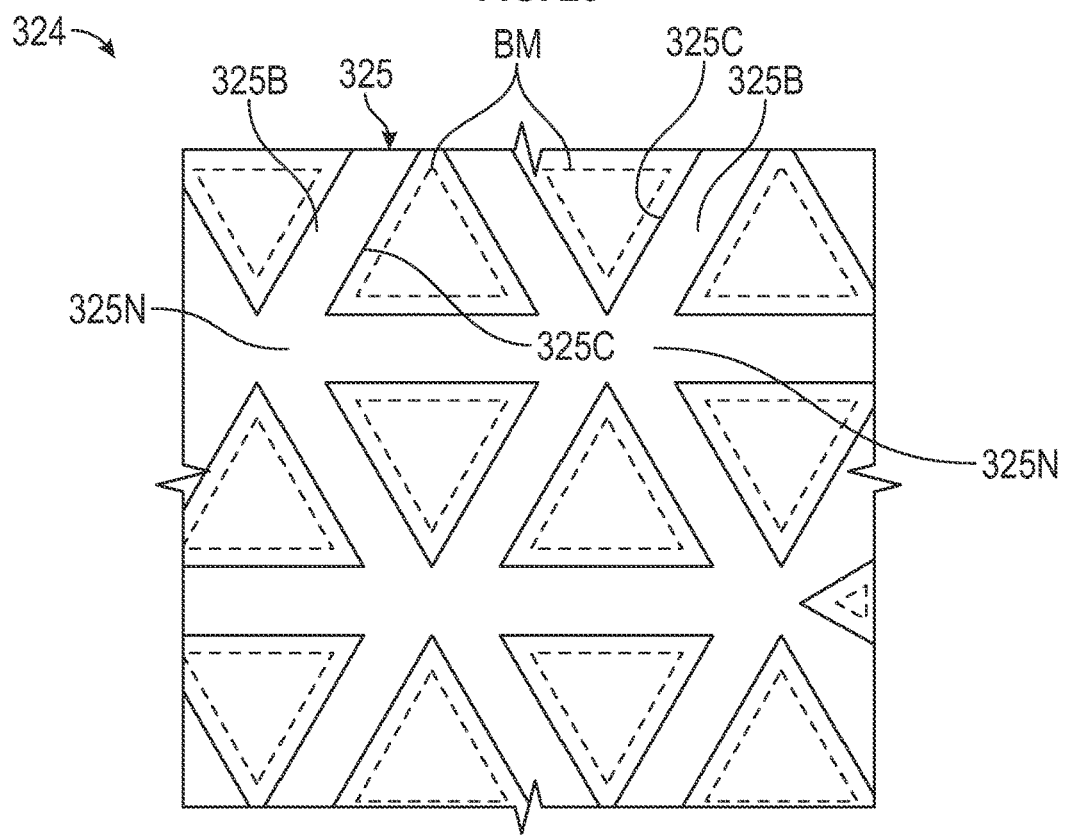
FIG. 29 illustrates an exemplary augment including a scaffold.

At step 300P, one or more operations can be performed to prepare or finish the implant 320. Referring to FIG. 29, biological material BM (shown in dashed lines for illustrative purposes) can be positioned in cavities 325C which may be established between the branches 325B and nodes 325N of the scaffold 325 of the augment 324.

Various techniques can be utilized to position the biological material BM. The biological material BM may injected or deposited into the cavities 325C under pressure. The biological material BM may be "scratch fit" along surfaces of the scaffold 325, such as moving the surfaces of the scaffold 325 relative to surfaces of another site such as within a cavity formed in a humeral head of the patient. The biological material BM may be printed in the cavities 325C during the printing step 300M. Embedding biological material BM in the scaffold 325 may improve healing at the surgical site.

Other example operations can include marking the implant with a respective identification code, such as an image upload number or customer order number. The implant can be laser marked with the identification code at step 300P or can be printed in the augment at step 300M, for example.

At step 300Q, a surgical site can be prepared for placement of the respective implant. Step 300Q can include placing one or more guide pins in the surgical site, reaming a surface of the surgical site, and/or drilling one or more holes in the surgical site which may be dimensioned to receive respective fasteners, for example.

Figure 30:
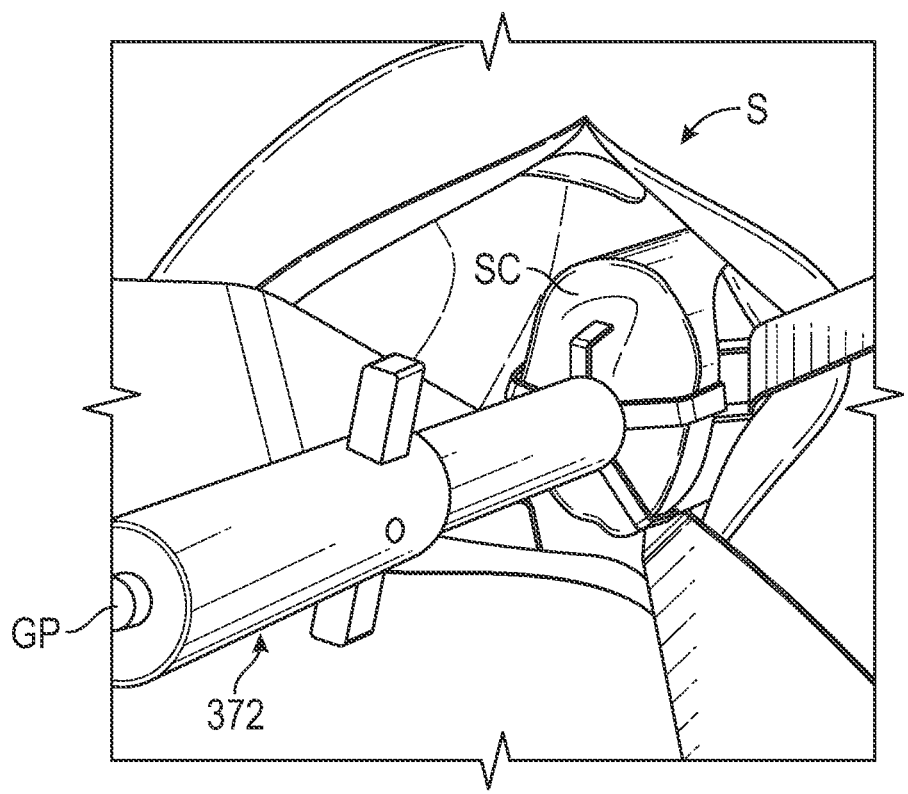
FIG. 30 illustrates placement of a guide pin according to an embodiment.

A patient-specific plan established utilizing the system 364 including the selected characteristics stored at step 300F can be utilized to set a position and trajectory of the guide pin, as illustrated by a tool 372 and guide pin GP in FIG. 30 (see also guide pin GP of FIG. 2).

Referring to FIG. 2, with continuing reference to FIG. 9, at step 300R the respective implant 20 may be positioned relative to the guide pin GP set during step 300Q and may be secured to the surgical site S. Step 300R can include moving the implant 20 along the guide pin GP in a direction D2 to position the augment 24 onto the conforming surface contour SC of the surgical site S.

Step 300R can include drilling a pilot hole for each respective fastener F in the tissue T which may be according to the patient-specific positions and trajectories. The implant 20 can be secured to the surgical site S with one or more fasteners F. Each fastener F may be inserted into an aligned pair of plate and augment apertures 36, 48 which may be according to a predetermined fastener type and length stored at step 300F before proceeding to next fastener F. Step 300R can include securing the glenosphere 56 to the plate body 26 adjacent to the front face 28 of the baseplate 22. A size and type of the glenosphere 56 can be selected at step 300A according to the patient-specific plan.

The novel implants and methods of this disclosure can provide versatility in design, manufacture and implant placement. The disclosed implants and augment geometries can be utilized to closely approximate a dimension of a bone surface and fill a bone void, which can lead to improved healing at the surgical site. Formation of the augments according to patient-specific geometries utilizing the techniques disclosed herein can reduce production and wait times. Apertures can be formed in the augments according to a selected trajectory of the fasteners based on a geometry of the surgical site, as well as bone quality and thickness. Forming the apertures during formation of the respective augment can reduce secondary machining operations such as drilling or reaming apertures into the augment, which can reduce manufacturing complexity and improve durability of the component. Augments having different geometries can be formed on standardized baseplate geometries that have previously passed quality assurance requirements and certification, which can focus quality assurance activities on the printed augments to ensure compliance of the overall implant. Scrap rates due to out-of-tolerance conditions may also be reduced.

Although the different non-limiting embodiments are illustrated as having specific components or steps, the embodiments of this disclosure are not limited to those particular combinations. It is possible to use some of the components or features from any of the non-limiting embodiments in combination with features or components from any of the other non-limiting embodiments.

The foregoing description shall be interpreted as illustrative and not in any limiting sense. A worker of ordinary skill in the art would understand that certain modifications could come within the scope of this disclosure. For these reasons, the following claims should be studied to determine the true scope and content of this disclosure.

What is claimed is:

1. A method of forming an orthopaedic implant for implanting in a patient comprising:
defining an augment volume associated with a respective baseplate, wherein the baseplate includes a plate body extending between front and rear faces and includes at least one plate aperture extending along an aperture axis between the front and rear faces, and wherein a void space in the augment volume is defined along a trajectory of the aperture axis;
printing an augment on the rear face of the respective baseplate according to the augment volume such that at least one augment aperture is established in the void space along the trajectory of the respective aperture axis, including moving a printing head across the rear face;
positioning the respective baseplate in a fixture such that the rear face is exposed; and
repeating the defining and printing steps for a first set of baseplates, and wherein the positioning step includes positioning the first set of baseplates at respective locations along the fixture.

2. The method as recited in claim 1, wherein the at least one plate aperture includes a plurality of plate apertures distributed along the rear face, and the at least one augment aperture includes a plurality of augment apertures aligned with respective ones of the plate apertures.

3. The method as recited in claim 2, wherein each of the plate apertures and a respective one of the augment apertures is dimensioned to receive a common fastener along the respective plate aperture axis.

4. The method as recited in claim 2, wherein the printing step includes establishing an augment body of the augment along the rear face and establishing an anchoring stem of the augment that extends outwardly from the augment body.

5. The method as recited in claim 4, wherein the printing step occurs such that the augment apertures are circumferentially distributed about a longitudinal axis of the anchoring stem.

6. The method as recited in claim 1, wherein the printing step occurs such that at least a portion of a medial face of the augment is transverse to the rear face, and the at least one augment aperture extends between the portion of the medial face and a lateral face of the augment disposed along the rear face of the plate body.

7. The method as recited in claim 6, wherein the rear face has a substantially planar geometry, and the aperture axis is non-perpendicular to the rear face.

8. The method as recited in claim 1, wherein the augment volume is defined between the rear face of the respective baseplate and a predefined surface contour of a bone surface.

9. The method as recited in claim 8, further comprising determining the predefined surface contour prior to the defining step, wherein the predefined surface contour is a patient-specific surface contour of a glenoid face.

10. The method as recited in claim 1, wherein the rear face has a substantially planar geometry.

11. The method as recited in claim 1, wherein the defining step occurs such that the augment volume associated with a baseplate of the first set of baseplates differs from the augment volume associated with another baseplate of the first set of baseplates.

12. The method as recited in claim 11, further comprising repeating the defining and printing steps for a second set of baseplates, the positioning step includes positioning the second set of baseplates at respective locations along the fixture, and the defining step occurs such that the augment volume is common to each augment corresponding to the second set of baseplates.

13. The method as recited in claim 1, wherein the plate body comprises a first material, the augment comprises a second material, and the printing step occurs such that a porosity of the second material differs from a porosity of the first material.

14. The method as recited in claim 13, wherein the printing step occurs such that augment includes a porous scaffold having an interconnected network of branches and nodes.

15. The method as recited in claim 14, further comprising positioning biological material in the porous scaffold.

16. The method as recited in claim 15, wherein the step of positioning the biological material in the porous scaffold includes printing the biological material in cavities established between the branches and the nodes of the porous scaffold.

17. The method as recited in claim 13, wherein the first material of the plate body is a metallic material.

18. The method as recited in claim 17, wherein the first material and the second material differ from each other in composition.

19. The method as recited in claim 1, further comprising securing a glenosphere to the plate body adjacent to the front face, wherein the glenosphere includes an articulating surface having a generally convex geometry.

20. The method as recited in claim 19, wherein the glenosphere includes a recess dimensioned to at least partially receive the plate body, the plate body includes a mounting portion establishing the front face, and a perimeter of the mounting portion is dimensioned to cooperate with a perimeter of the recess to establish a Morse taper connection.

* * * * *